(12) United States Patent
Doepker et al.

(10) Patent No.: US 11,944,767 B2
(45) Date of Patent: *Apr. 2, 2024

(54) WIRE LOCK ASSEMBLY

(71) Applicant: Cook Medical Technologies LLC, Bloomington, IN (US)

(72) Inventors: Bradley R. Doepker, Troy, OH (US); Michelle D. Martinez, Winston-Salem, NC (US); Tyler Evans McLawhorn, Winston-Salem, NC (US); John C. Sigmon, Jr., Winston-Salem, NC (US); Shaun Gittard, Winston-Salem, NC (US); Michael Brecht, Salisbury, NC (US); Maximiliano Soetermans, Pinnacle, NC (US)

(73) Assignee: Cook Medical Technologies LLC, Bloomington, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/593,000

(22) Filed: Feb. 4, 2022

(65) Prior Publication Data

US 2022/0152360 A1 May 19, 2022

Related U.S. Application Data

(63) Continuation of application No. 15/584,162, filed on May 2, 2017, now Pat. No. 11,253,680.
(Continued)

(51) Int. Cl.
*A61M 25/09* (2006.01)
*A61B 1/00* (2006.01)
(Continued)

(52) U.S. Cl.
CPC ... *A61M 25/09041* (2013.01); *A61B 1/00133* (2013.01); *A61B 17/0218* (2013.01);
(Continued)

(58) Field of Classification Search
CPC ............ A61M 25/09041; A61M 25/09; A61M 25/09125; A61B 17/0218; A61B 17/0469;
(Continued)

(56) References Cited

U.S. PATENT DOCUMENTS 4,000,739 A   1/1977 Stevens
4,143,853 A   3/1979 Abramson
(Continued)

FOREIGN PATENT DOCUMENTS

JP   2007-500559   1/2007
JP   2010-511440   4/2010

OTHER PUBLICATIONS

Chinese Application No. 2017800343130 Second Office Action dated Jun. 15, 2021, English translation.
(Continued)

*Primary Examiner* — Marcela I. Shirsat
(74) *Attorney, Agent, or Firm* — Crowell & Moring LLP

(57) ABSTRACT

A wire lock assembly for an access port of an elongate medical tube includes a body having an exterior surface, an interior surface, and a central opening disposed therethrough, an attachment mechanism disposed through the exterior surface of the body, the attachment mechanism having an open end and a closed end, at least one notch arranged on the body and positioned proximate to the central opening and at least one seal supported within the interior surface of the body in communication with the central opening, the seal comprising a passageway therethrough, where the interior surface of the body defines a non-linear pathway for securing one or more medical devices.

18 Claims, 22 Drawing Sheets

Related U.S. Application Data

(60) Provisional application No. 62/490,958, filed on Apr. 27, 2017, provisional application No. 62/331,083, filed on May 3, 2016.

(51) Int. Cl.

| | |
|---|---|
| *A61B 1/018* | (2006.01) |
| *A61B 17/02* | (2006.01) |
| *A61B 17/12* | (2006.01) |
| *A61B 17/32* | (2006.01) |

(52) U.S. Cl.
CPC .......... *A61M 25/09* (2013.01); *A61B 1/00137* (2013.01); *A61B 1/0014* (2013.01); *A61B 1/018* (2013.01); *A61B 17/12013* (2013.01); *A61B 17/320016* (2013.01); *A61M 2025/09125* (2013.01)

(58) Field of Classification Search
CPC .......... A61B 17/12013; A61B 17/1285; A61B 17/320016; A61B 17/1714; A61B 17/1728; A61B 17/1757; A61B 1/00137; A61B 1/018; F16L 3/04; F16L 3/08; F16L 3/10; F16L 3/12; F16L 3/2235
USPC .......... 600/154, 201; 24/339; 248/68.1, 74.1, 248/73, 65; 606/96–98, 103–104, 86 R
See application file for complete search history.

(56) References Cited

U.S. PATENT DOCUMENTS

| | | | |
|---|---|---|---|
| 4,198,959 A | 4/1980 | Otani | |
| 4,430,081 A | 2/1984 | Timmermans | |
| 4,610,665 A | 9/1986 | Matsumoto et al. | |
| 4,735,614 A | 4/1988 | Yapp et al. | |
| 4,844,092 A | 7/1989 | Rydell et al. | |
| 4,988,356 A | 1/1991 | Crittenden et al. | |
| 5,046,497 A | 9/1991 | Millar | |
| 5,125,905 A | 6/1992 | Wright et al. | |
| 5,159,861 A | 11/1992 | Anderson | |
| 5,281,203 A | 1/1994 | Ressemann | |
| 5,312,338 A | 5/1994 | Nelson et al. | |
| 5,325,746 A | 7/1994 | Anderson | |
| 5,325,868 A | 7/1994 | Kimmelstiel | |
| 5,342,292 A | 8/1994 | Nita et al. | |
| 5,423,331 A | 6/1995 | Wysham | |
| 5,443,078 A | 8/1995 | Uflacker | |
| 5,453,097 A | 9/1995 | Paradis | |
| 5,575,711 A | 11/1996 | Walinsky | |
| 5,579,779 A | 12/1996 | Humphrey | |
| 5,579,780 A | 12/1996 | Zadini et al. | |
| 5,658,309 A | 8/1997 | Berthiaume et al. | |
| 5,730,150 A | 3/1998 | Peppel et al. | |
| 5,762,070 A | 6/1998 | Nagamatsu | |
| 5,769,786 A | 6/1998 | Wiegel | |
| 6,059,484 A | 5/2000 | Grieive | |
| 6,096,009 A | 8/2000 | Windheuser et al. | |
| 6,126,633 A | 10/2000 | Kaji et al. | |
| 6,280,432 B1 | 8/2001 | Turovskiy et al. | |
| 6,312,404 B1 | 11/2001 | Agro et al. | |
| 6,346,093 B1 | 2/2002 | Allman et al. | |
| 6,450,976 B2 | 9/2002 | Korotko et al. | |
| 6,517,518 B2 | 2/2003 | Nash et al. | |
| 6,520,951 B1 | 2/2003 | Carrillo, Jr. et al. | |
| 6,533,782 B2 | 3/2003 | Howell et al. | |
| 6,595,982 B2 | 7/2003 | Sekino et al. | |
| 6,663,597 B1 | 12/2003 | Windheuser et al. | |
| 6,679,872 B2 | 1/2004 | Turovskiy et al. | |
| 6,746,466 B2 | 6/2004 | Eidenschink et al. | |
| 6,827,683 B2 | 12/2004 | Ottawara | |
| 6,827,718 B2 | 12/2004 | Hutchins et al. | |
| 8,246,585 B2 | 8/2012 | Schennib | |
| 8,388,521 B2 | 3/2013 | Byers et al. | |
| 8,850,676 B2 | 10/2014 | Schmitt | |
| 8,905,920 B2 | 12/2014 | Meloul | |
| 11,253,680 B2 * | 2/2022 | Doepker ............ A61B 1/00133 |
| 2002/0087100 A1 | 7/2002 | Onuki et al. | |
| 2002/0177869 A1 | 11/2002 | Eidenschink et al. | |
| 2003/0088153 A1 | 5/2003 | Carrillo et al. | |
| 2004/0106852 A1 | 6/2004 | Windheuser et al. | |
| 2004/0162465 A1 | 8/2004 | Carrillo | |
| 2005/0090835 A1 | 4/2005 | Deal | |
| 2006/0195117 A1 * | 8/2006 | Rucker ........... A61M 25/09041 |
| | | | 606/108 |
| 2009/0088600 A1 | 4/2009 | Meloul | |
| 2010/0174139 A1 | 7/2010 | Windheuser et al. | |
| 2012/0323146 A1 | 12/2012 | Eden | |
| 2016/0089007 A1 | 3/2016 | Weitzner et al. | |
| 2016/0235277 A1 | 8/2016 | Kudo | |

OTHER PUBLICATIONS

Chinese Application No. 2017800343130 First Office Action dated Aug. 21, 2020, English translation.
Japanese Application No. 2018-557849 Second Office Action dated May 25, 2021, English translation.
Japanese Application No. 2018-557849 Second Office Action dated Nov. 5, 2019, English translation.
Eurpoean Application No. 21159090.6 Search Report dated May 27, 2021.
Examination Report No. 2 for AU Application No. 2017259964 dated Jul. 17, 2019.
Examination Report No. 1 for AU Application No. 2017259964 dated Jan. 16, 2019.
Communication pursuant to Rules 161(1) and 162 EPC for EP Application No. 17723826.8 dated Dec. 11, 2018.
International Preliminary Report on Patentability for International Application No. PCT/US2017/030550 dated Nov. 15, 2018.
International Search Report for International Application No. PCT/US2017/030550 dated Jul. 10, 2017.
Japanese Application No. 2022-000544 Notice of Grounds of Rejection dated Oct. 25, 2022, English translation (5 pp.).
First Office Action dated Nov. 22, 2023 in China Application No. 2023112200001900 (English and Chinese languages) (9 pp.).

* cited by examiner

WIRE LOCK ASSEMBLY

The present application is a continuation application that claims priority to U.S. Utility patent application Ser. No. 15/584,162 application, filed May 2, 2017 and entitled "Wire Lock Assembly, which claims the benefit of priority from U.S. Provisional Application No. 62/331,083, filed May 3, 2016 and U.S. Provisional Application No. 62/490,958, filed Apr. 27, 2017, each of which are hereby incorporated by reference.

BACKGROUND

The invention is useful in the area of medical procedures, particularly medical procedures involving an introducer catheter, a wire guide, an endoscope, or the like.

Endoscopes are routinely used to perform various medical procedures in areas of the body that are difficult to visualize, access, or that may otherwise require an open procedure to access. Further, in many cases, endoscopes allow visual access to a target anatomy without the use of radioactive fluoroscopy. Endoscopes also provide a working channel for other devices to be passed through the endoscope and directly target an internal body lumen or area of the anatomy. For example, catheters, wire guides and other types of elongated medical devices are frequently pass through the working channel of an endoscope to perform a diagnostic or medical procedure at a location near the distal end of the endoscope.

Wire guides are used during many procedures in the gastrointestinal system, including the pancreatobiliary system (i.e., the biliary tree), the stomach, and the esophagus. Wire guides are long, slender, relatively flexible wires that are used to gain and maintain access to the body's narrow passageways during minimally invasive medical procedures. Because of the substantial length of wire guides, they can be cumbersome and require constant, delicate manipulation by a physician.

Wire guides often must be maintained in a stationary position relative to the patient where a physician performs various procedures. In particular, maintaining the wire guide in a stationary position is important to prevent loss of access to a target anatomy, for example, a duct in the biliary tree. Also, during an esophageal dilation, a physician must secure a wire guide within the esophagus and across an esophageal stricture as one of more dilators are advanced over the wire guide. Likewise, during a percutaneous endoscopic gastrostomy (PEG) to placement, a wire guide must be secured relative to the patient's mouth, esophagus, and stomach as a physician inserts a feeding tube.

Due to the complexity of these procedures, physicians often need the assistance of another person to hold the endoscope, manipulate the catheter, and/or hold the wire guide. However, this shifts the focus of the assistant from there other areas of responsibility, such as checking the patient, checking monitors for relevant information, or carrying out other task. As such, it is desirable to design a medical device that addresses these considerations.

BRIEF SUMMARY

In one aspect, a wire lock assembly for an access port of an elongate medical tube includes a body having an exterior surface, an interior surface, and a central opening disposed therethrough, an attachment mechanism disposed through the exterior surface of the body, the attachment mechanism having an open end and a closed end, at least one notch arranged on the body and positioned proximate to the central opening and at least one seal supported within the interior surface of the body in communication with the central opening, the seal comprising a passageway therethrough, where the interior surface of the body defines a non-linear pathway for securing one or more medical devices. In some embodiments, the one or more medical devices comprises a wire guide. In other embodiments, the non-linear pathway of the interior surface is defined by one or more bends and the one or more medical devices are locked in place by a sliding motion in which the one or more medical device assumes the non-linear pathway by bending. In additional embodiments, the attachment mechanism comprises a ramp and a snap-fit mechanism positioned distal to the ramp. A ledge may be proximally disposed about the periphery of the attachment mechanism. In some embodiments, the medical device further comprises at least one slot for engaging an end of an elongate medical device. The interior surface of the non-linear path may be formed between the top section and the intermediate section of the body. A pair of snap-fit mechanisms may be positioned within the non-linear pathway. In alternative embodiments the internal surface of the body forces the one or more medical devices into a bent state.

In another aspect, a wire lock assembly includes a body having an exterior surface, an interior surface, and a central opening disposed therethrough, an attachment mechanism disposed through the exterior surface of the body, the attachment mechanism having an open end and a closed end, at least one seal supported within the interior surface of the body in communication with the central opening, the seal comprising a passageway therethrough, and one or more tail lock passages disposed through the body transverse to the central opening, the one or more tail lock passages comprising an angled interior surface; where the interior surface of the body defines a non-linear pathway formed between the top section and the intermediate section of the body for securing one or more medical devices. In some embodiments, the attachment mechanism has a U-shaped configuration.

In another aspect, a system for holding a wire guide, includes an endoscope having an access port; a wire lock assembly affixed to the access port, the medical device comprising a body having an exterior surface, an interior surface, and a central opening disposed therethrough and tail lock passages disposed through the body transverse to the central opening, the one or more tail lock passages comprising an angled interior surface, wherein the interior surface of the body defines a non-linear pathway for securing a wire guide.

DETAILED DESCRIPTION OF THE DRAWINGS AND THE PRESENTLY PREFERRED EMBODIMENTS

Figure 1A:
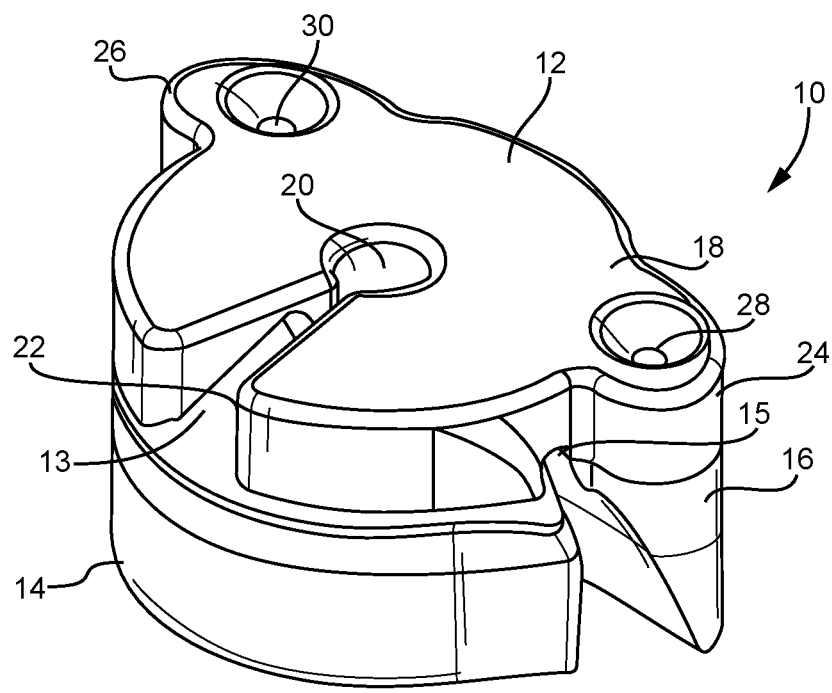
FIG. 1A illustrates a front perspective view an embodiment of a wire lock assembly.

The invention is described with reference to the drawings in which like elements are referred to by like numerals. The relationship and functioning of the various elements of this invention are better understood by the following detailed description. However the embodiments of this invention as described below by way of example only, and the invention is not limited to the embodiments illustrated in the drawings. It should also be understood that the drawings are not to scale and in certain instances details have been omitted, which are not necessary for an understanding of the present invention, such as conventional details of fabrication and assembly.

Unless otherwise defined, all technical and scientific terms used herein have the same meaning as commonly understood by one of ordinary skill in the art to which this invention pertains. In case of conflict, the present document, including definitions, will control. Preferred methods and materials are described below, although methods and materials similar or equivalent to those described herein can be used in the practice or testing of the present invention. The materials, methods, and examples disclosed herein are illustrative only and not intended to be limiting.

The terms "comprise(s)," "include(s)," "having," "has," "can," "contain(s)," and variants thereof, as used herein, are intended to be open-ended transitional phrases, terms, or words that do not preclude the possibility of additional acts or structures. The present invention also contemplates other embodiments "comprising," "consisting of and "consisting essentially of," the embodiments or elements presented herein, whether explicitly set forth or not.

The terms "about" or "substantially" used with reference to a quantity includes variations in the recited quantity that are equivalent to the quantity recited, such as an amount that is insubstantially different from a recited quantity for an intended purpose or function.

The term "endoluminal" refers to or describes the internal or inside of a lumen, duct, and other passageways or cavities located in a human or other animal body. A lumen or a body passageway may be an existing lumen or a lumen created by surgical intervention. As used in this specification, the terms "lumen" or "body passageway," and "vessel" are intended to have a broad meaning and encompass any duct (e.g., natural or iatrogenic) or cavity within the human body and may include, without limitation, urethral and ureteral passages, blood vessels, respiratory ducts, gastrointestinal ducts, such as the biliary duct, intestines, the esophagus, the pericardial cavity, the thoracic cavity, and the like. Accordingly, the terms "endoluminal device" or "endoluminal prosthesis" describe devices that can be placed inside or moved through any such lumen or duct.

The terms "patient," "subject," and "recipient" as used in this application may refer to any animal, particularly humans.

The term "medical device" means any object that is itself or that includes a component that is intentionally inserted into the body of a patient as part of a medical treatment, and that comprises a structure adapted for introduction into a patient. The medical device can be a tool, such as, without limitation, a catheter, a wire guide, a forceps, or a scissors used to affect a surgical procedure at and/or deliver a second medical device to a treatment site in a patient.

The terms "proximal" and "distal" will be used to describe opposing axial ends of the wire lock, as well as the axial ends of various component features. The term "proximal" is used to refer to the end of the medical device (or component thereof) that is closest to the operator during use of the system. The term "distal" is used to refer to the end of the medical device (or component thereof) that is initially inserted into the patient, or that is closest to the patient during use.

The term "ramp" will be used to describe a slope or inclined plane tilted at an angle, with one end higher than the other, used to connect one surface to another surface. The term "ramp" is intended to broad meaning may have varying slope, where the slope is equal to the difference in height between its two ends, or rise, divided by its horizontal length, or run. The "ramp" may have a linear or non-linear configuration.

A more detailed description of the embodiments will now be given with reference to FIGS. 1A-35. The present invention is not limited to those embodiments illustrated; it specifically contemplates other embodiments not illustrated but intended to be included in the claims.

In general, FIG. 1A illustrates an embodiment of a wire lock assembly 10. In this embodiment, the wire lock assembly 10 comprises a body 12 having a generally hemispherical shape. The body 12 of the wire lock assembly 10 may be molded to a particular form, where the wire lock assembly has a bottom section 14, intermediate section 16, and a top section 18. However, in alternative embodiments, the body 12 of the wire lock assembly 10 may comprise other geometric structures. As shown in this embodiment, a central pathway 20 is disposed through the body 12 of the wire lock assembly 10, defining a pathway for a wire guide, catheter, or similar type of elongate medical device (hereinafter collectively referred to as a "wire guide"). Within the body 12 of the wire lock assembly is a non-linear wire guide locking pathway 13 leading to a wire guide locking slot 15 for a wire guide. When the wire lock assembly 10 is attached to a medical device, such as an endoscope, a wire guide extending through the working channel of the medical device may also extend through the central pathway 20. In this position, a wire guide can be placed in the non-linear wire guide locking pathway 13. The body 12 of the wire lock assembly 10 includes a notch 22 disposed through the top section 18 of the body 12. The notch 22 helps to facilitate the positioning of the wire guide in the non-linear wire guide locking pathway formed within the body 12 of the wire lock assembly 10.

The body 12 of the wire lock assembly 10 further includes two side wings 24, 26 comprising wire guide tail locks 28, 30. The side wings 24, 26 enable the user to have a surface to grasp in order to attach and detach the wire lock assembly 10 from the port of a medical device. As shown, the side wings 24, 26 have a generally rounded surface. However, one ordinary skill in the art would understand that other configurations may be used with the side wings. The wire guide tail locks 28, 30 are disposed through the body 12 of the wire lock assembly 10 and are positioned on opposing sides of the body 12 of the wire lock assembly 10. In some embodiments, the wire guide tail locks 28, 30 may comprise one opening or a plurality of openings. The wire guide tail locks 28, 30 enable the locked wire guide to be looped over the body 12 of the wire lock assembly 10 and locked in a downward or upward position.

Figure 1B:
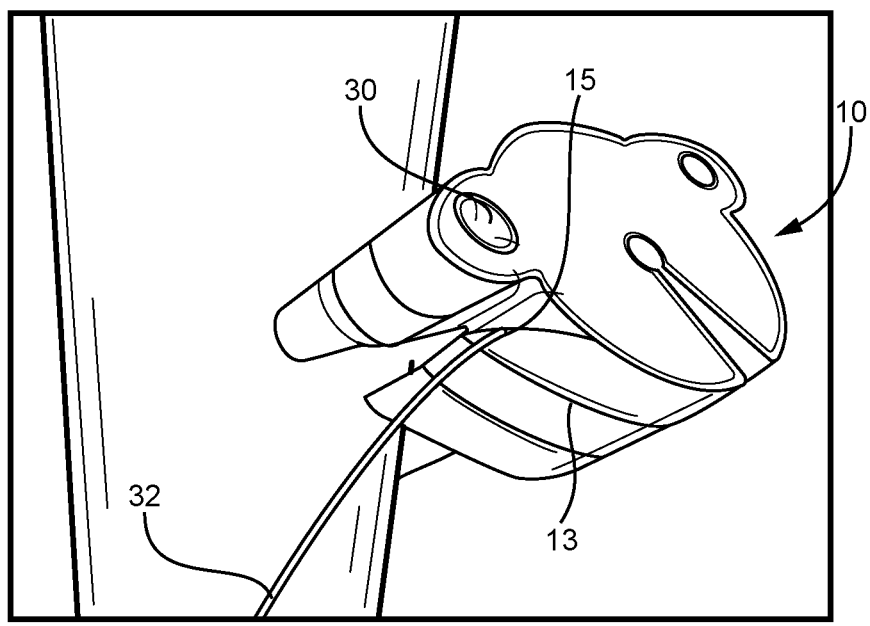
FIG. 1B illustrates a wire guide positioned within a wire guide locking slot of a wire lock assembly.

FIG. 1B illustrates an exemplary embodiment of the wire lock assembly where a wire guide 32 is positioned within the non-linear pathway 13 and the wire guide locking slot 15. In this locked position, the non-linear pathway 13 and wire guide locking slot 15 induces a three point bend to the wire guide 32 wherein the wire guide is automatically placed in a locked position. As will be discussed below, the configuration of the non-linear wire guide locking track prevents the wire guide from being damaged, as the wire guide is not pinched between opposing surface of the wire guide locking path. Further, after traversing the wire guide locking pathway 13 and is positioned within the wire guide locking slot 15, the wire guide is in an automatically locked position.

Figure 1C:
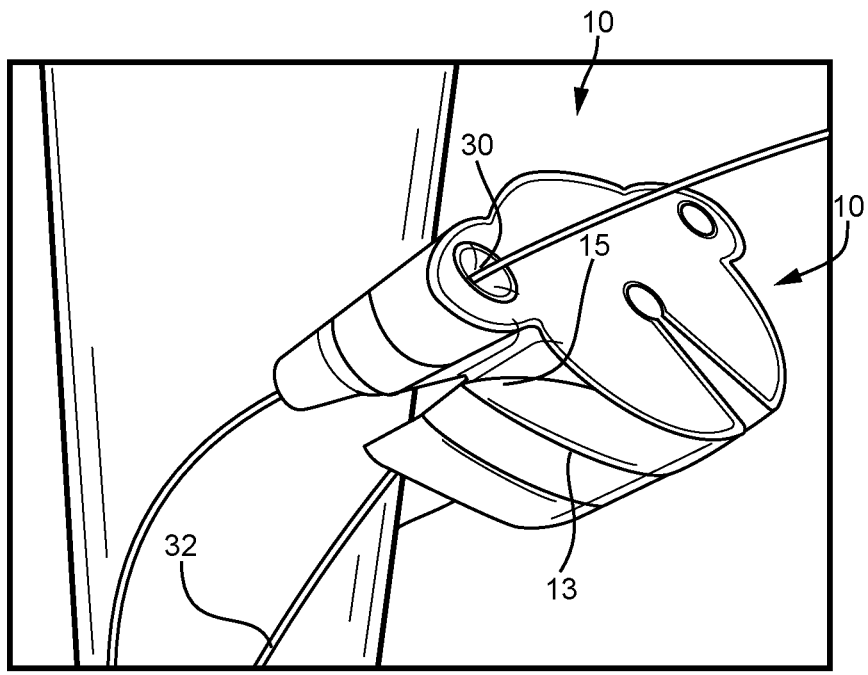
FIG. 1C illustrates a wire guide positioned within a wire guide docking slot of a wire lock assembly.

FIG. 1C illustrates a wire guide 32 positioned within a wire guide docking slot 30. As shown in FIG. 1C, an end of a wire guide 32 is secured in a position which may prevent inadvertent contact with a loose guide wire. During use, the wire guide may be placed on either side of the wire lock assembly in order to increase the space available to the user to adjust the device(s) in use with the wire lock.

Figure 2:
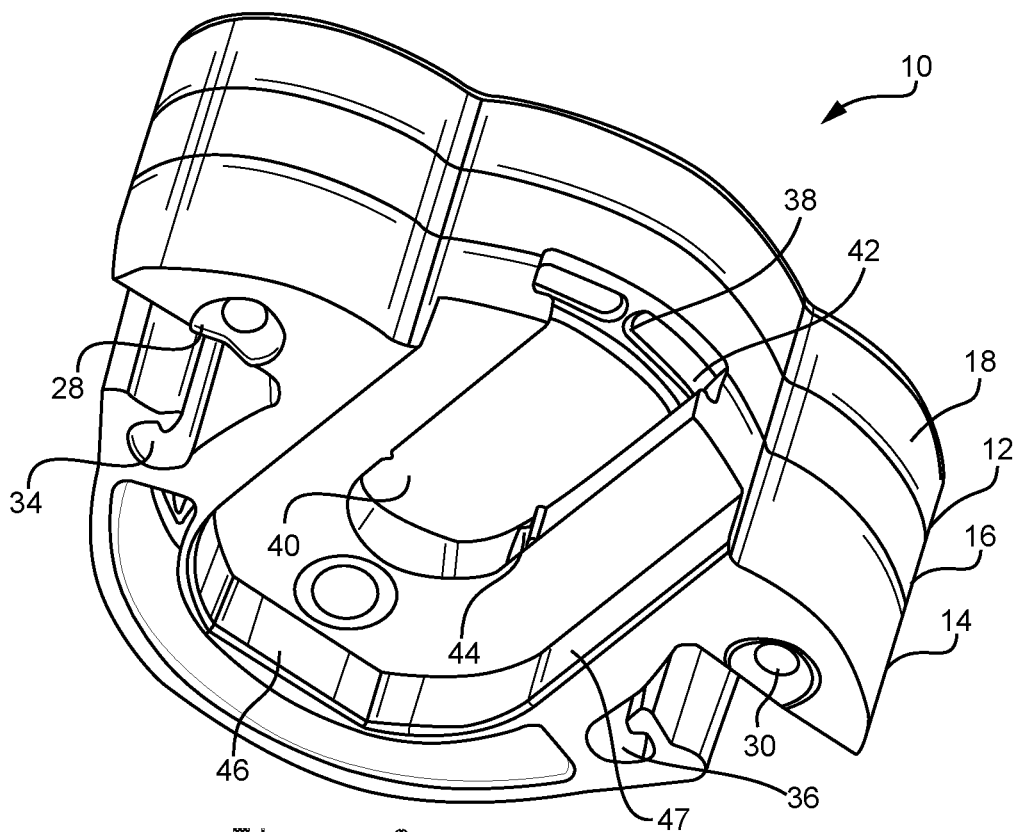
FIG. 2 illustrates a back perspective view of an embodiment of a wire lock assembly.

FIG. 2 illustrates a back perspective view of the wire lock assembly 10. As shown, the wire lock assembly 10 includes a pair of wire guide docking slots 28, 30 on opposing sides, a pair of secondary wire guide locks 34, 36, an attachment mechanism 38, and a seal 40 disposed within the body 12 of the wire lock assembly 10. The attachment mechanism 38 facilitates connection between the wire lock assembly 10 and a port of a second medical device. In this embodiment, the attachment mechanism 38 is configured to engage with a port of an endoscope. As shown, the attachment mechanism 38 includes a groove 42 formed through the bottom section 14 of the wire lock assembly 10. A securing mechanism, such as a snap-fit locking mechanism 44, is provided within the groove 42 of the attachment mechanism 38 in order to provide for a more secure fit between the medical device and the port of the second medical device. Alternative embodiments may comprise other types of securing mechanism, including, but not limited to, friction based, press-fit, mechanical fasteners, and plastic threads. A ledge 46, having a thickness with respect to the body 12 of the wire lock assembly 10, is positioned beneath the attachment mechanism 38. In this embodiment, the ledge 46 has a semi-hemispherical configuration and includes edges 47 which expand beyond the outer perimeter of the groove 42 of the attachment mechanism 38. The ledge 46 helps to prevent unwanted rotation of the wire lock assembly relative to a housing of the second medical device. The dimensions of the attachment mechanism 38 and the ledge 46 may be modified based on the dimensions of the second medical device.

The seal 40 is fluidly engaged with the central pathway 20 of the wire lock assembly 10 and is configured to limit the escape of any fluids that may be present within a working channel of a second medical device without inhibiting the insertion or movement of wire guides, catheters, or similar elongate devices. This configuration can be of particular benefit in preventing bodily fluids such as bile and blood from escaping and contaminating the physician and the working environment. The design and configuration of the seal 40, including the types of materials from which it may be manufactured, are well known to those skilled in the art. In this embodiment, the seal 40 is positioned between the bottom portion 14 and the intermediate portion 16 of the wire lock assembly 10. While an exemplary seal 40 may include a single slit, other types of slits, torn holes, arranged slits, or penetrable seals may alternatively be used. For example, other seal configurations include duckbill, membrane with slit (e.g., polystyrene, silicone, or another compliant polymer material), or other designs having the ability to seal around the catheter and wire guide to prevent any proximally migrating fluid from exiting the channel. The seal 40 in this embodiment is comprised of two generally flat surfaces.

Referring back to FIG. 2, two secondary wire guide locks 34, 36 are located proximate to the wire guide docking slots 28, 30 of the wire lock assembly 10 and disposed on the bottom section 14 of the wire lock assembly 10. As shown, the secondary wire guide locks 34, 36 comprise clamps having a generally c-shaped design. In alternative embodiments, other configurations may be suitable. In use, when the wire guide is locked in an outward position within the wire guide locking slot, a proximal portion of the wire guide may be placed within one of the secondary wire guide locks 34, 36 in a direction away from the user. The positioning of a proximal portion of the wire guide within one of the secondary wire guide locks 34, 36 provides a secondary lock for the wire guide, as the wire guide is placed into a locked position automatically upon being positioned within the wire guide locking slot 15.

Figure 3:
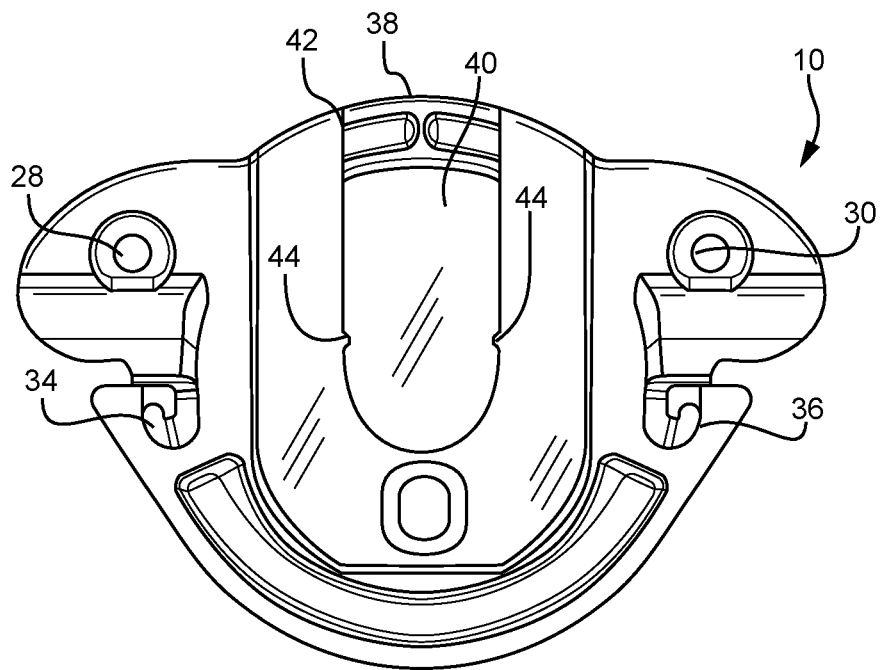
FIG. 3 illustrates a bottom view of an embodiment of a wire lock assembly.

FIG. 3 illustrates a bottom view of the wire guide lock assembly 10. As shown, the wire guide locking assembly 10 includes a pair of tail locks 28, 30 on opposing sides, a pair of secondary wire locks 34, 36, an attachment mechanism 38, and a seal 40 disposed within the body 12 of the wire lock assembly 10. A snap-fit locking mechanism 44 is provided within the groove 42 of the attachment mechanism 38 in order to provide for a more secure fit between the medical device and the port of the second medical device. A ledge 46, having a thickness with respect to the body 12 of the wire lock assembly 10, is positioned beneath the attachment mechanism 38. The seal 40 is configured to limit the escape of any fluids that may be present within a working channel of the second medical device without inhibiting the insertion or movement of wire guides, catheters, or similar elongate devices.

Figure 4:
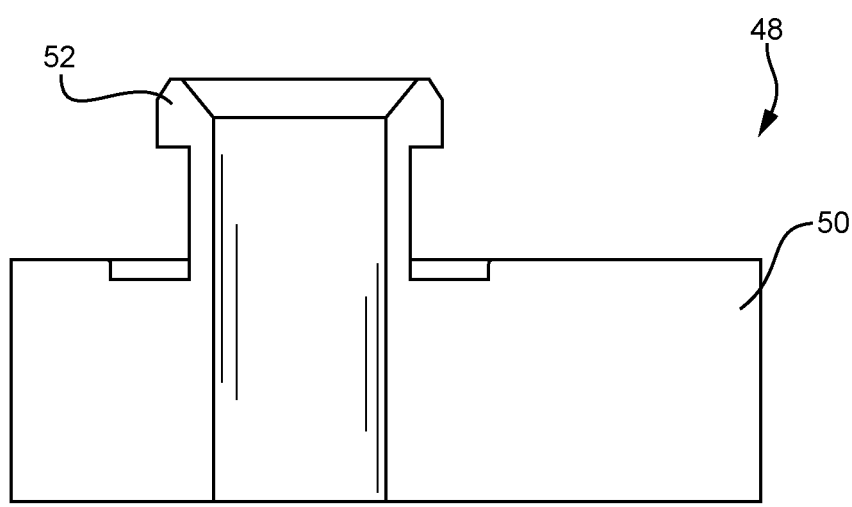
FIG. 4 illustrates an embodiment of an access port.

FIG. 4 illustrates a cross-section of an exemplary access port 48 of an endoscope. The access port 48 provides access to a working channel (not shown) that extends distally through the interior of the endoscope. The metal insert 48 may be covered by an access port cover, which may be removed to access the access port in the metal insert. The access port 48 comprises of a base 50 and a stem 52 having a height and width. In some embodiments, the access port 48 has a generally t-shaped configuration. One of skill will understand that ports having other types of configuration may also be used.

Figure 5:
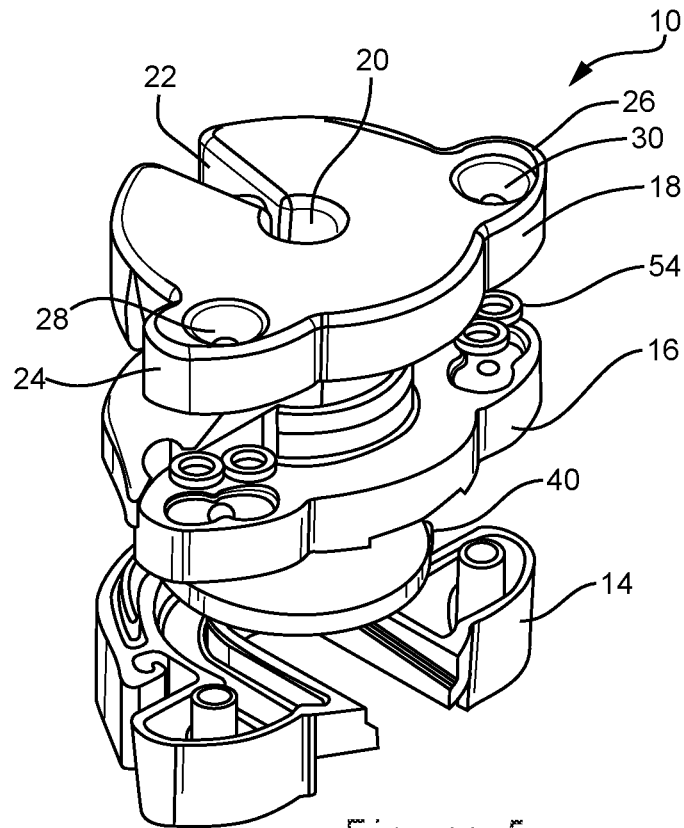
FIG. 5 illustrates an exemplary embodiment of a disassembled wire lock assembly.

FIG. 5 illustrates an exemplary embodiment of a disassembled wire lock assembly 10. The wire lock assembly 10 is in three pieces formed of a suitable material such as plastic. The materials may be molded to a particular form, where the wire lock assembly 10 has a bottom section 14, intermediate section 16, and a top section 18. The seal 40 is provided within the body 12 of the wire lock assembly 10. In this embodiment, the seal 40 is secured between the intermediate section 16 and the bottom section 14 of the wire lock assembly 10 and in fluid communication with the central pathway 20 of the wire lock assembly 10. O-rings 54 are positioned in the area surrounding a wire guide tail lock 28, 30 on opposing sides of the wire lock assembly 10. The intermediate section 16 and the top section 18 may include molded regions to receive the O-rings 54 within the body of the wire lock assembly 10. The O-rings 54 provide the user some tactile feedback and friction while placing a wire guide within one of the wire guide tail locks 28, 30. In this embodiment, a pair of O-rings 54 is positioned proximate to each wire guide tail lock. In alternative embodiments, differing combinations of O-rings may be used. In further alternative embodiments, other mechanical gaskets may be used to provide tactile feedback and friction to the user. Although the exemplary embodiment illustrated here is constructed by three pieces snap fit together, the wire lock assembly 10 may be made from one or more pieces that may be affixed together in any way. For example, pieces may be ultrasonically bonded, heat bonded, glued together, or affixed in any other way.

Figure 6:
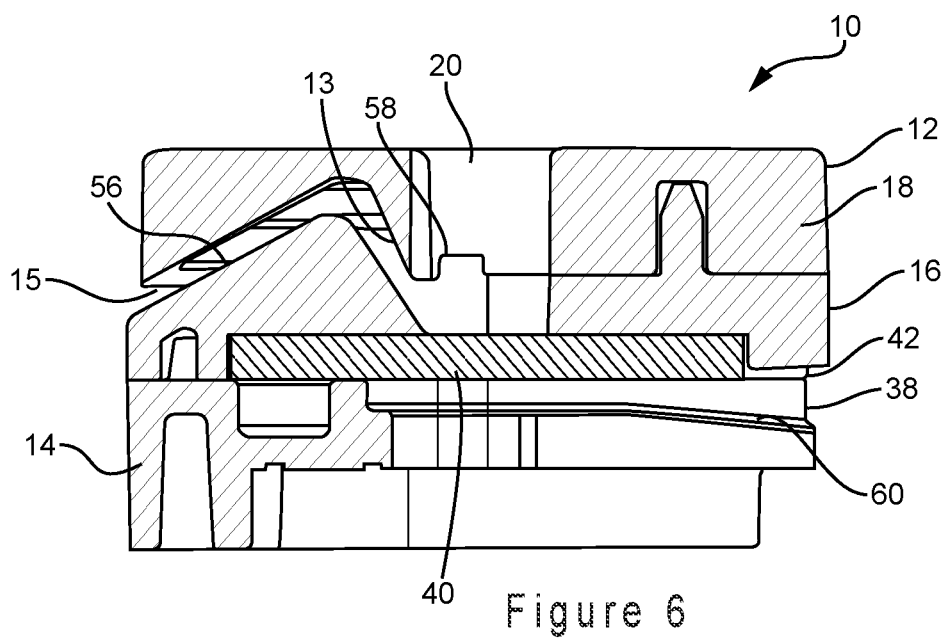
FIG. 6 illustrates a cross-sectional view an embodiment of a wire lock assembly.

FIG. 6 shows a cross-sectional view of the wire lock assembly 10. As shown, the wire lock assembly 10 includes a central pathway 20, an attachment mechanism 38, and a seal 40 disposed within the body 12 of the wire lock assembly 10. The top portion 18 and the intermediate portion 16 of the wire lock assembly form a wire guide locking path 13 leading to the wire locking slot 15. The wire guide locking path 13 includes a raised surface 56 that is positioned on the intermediate section 16 of the wire lock assembly. The raised rounded surface 56 extends about the periphery of the central pathway 20 and has a generally semi-hemispherical shape. As shown, the raised rounded surface includes a taper extending from central pathway 20 to the outer periphery of the intermediate section 16. The tapered section of the raised rounded surface 56 increases in diameter as it expands toward the outer periphery of the intermediate section 16. The raised rounded surface 56 includes a tapered, generally rounded surface that extends about the periphery of the intermediate opening. The wire lock assembly 10 further includes a flattened edge 58 positioned on the intermediate section 16 of the wire lock assembly. When the wire guide is secured in the wire guide locking slot, the flattened edge 58 may be used as a wedge between the wire guide and the catheter when the user pulls upward on the catheter in order to perform a catheter exchange. Within the groove 42 of the attachment mechanism 38 of the wire lock assembly 10 is an angled ramp 60. The angled ramp 60 allows the wire lock assembly 10 to be secured to a second medical device by sliding the wire lock assembly 10 onto a port of the second medical device.

Figure 7A:
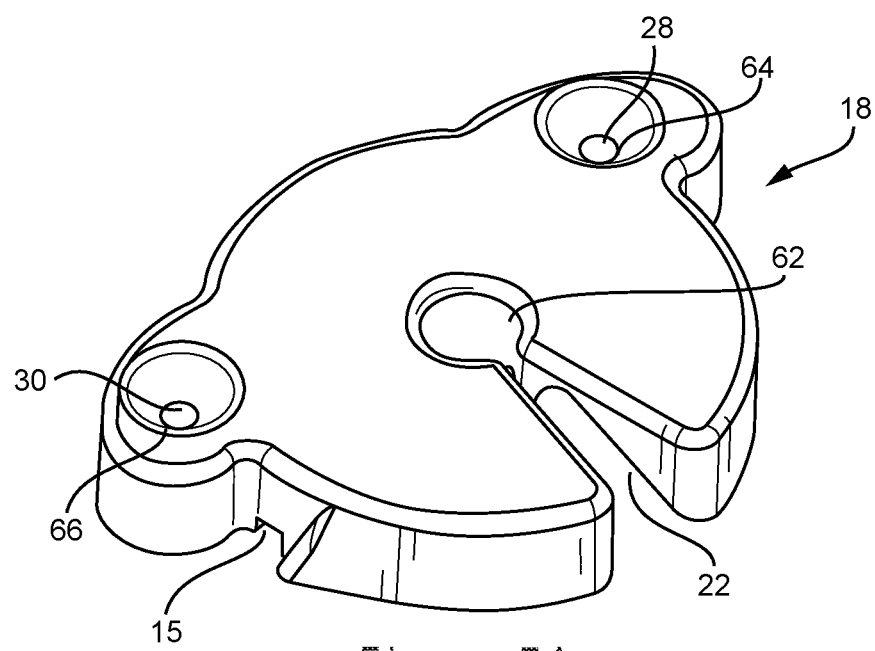
FIGS. 7A and 7B illustrates a top section of an embodiment of a wire lock assembly.

FIG. 7A shows a perspective view of an exterior surface of the top section 18 of the wire lock assembly 10. A top opening 62 is disposed through the exterior surface of the top section 18. The top opening 62 forms the entrance of the central pathway 20 of the body 12 of the wire lock assembly. A notch 22 of the wire lock assembly 10 is shown in fluid combination with the top opening 62. As shown, the notch 22 has a generally triangular shaped configuration. However, a skilled artisan understands that other suitable configurations may also be used to form the notch 22. The notch 22 helps to facilitate the positioning of the wire guide in a non-linear wire guide locking track formed within the body of the wire lock assembly. The dimensions of the notch 22 of the wire lock assembly 10 may be determined based on the dimensions of the wire guide or other medical device that will be used in conjunction with the wire lock assembly. Openings 64, 66 for wire guide tail locks 28, 30 are disposed through the top section 18 and are positioned on opposite sides. A wire guide locking slot 15 is positioned on an outer edge of the wire lock assembly 10.

Figure 7B:
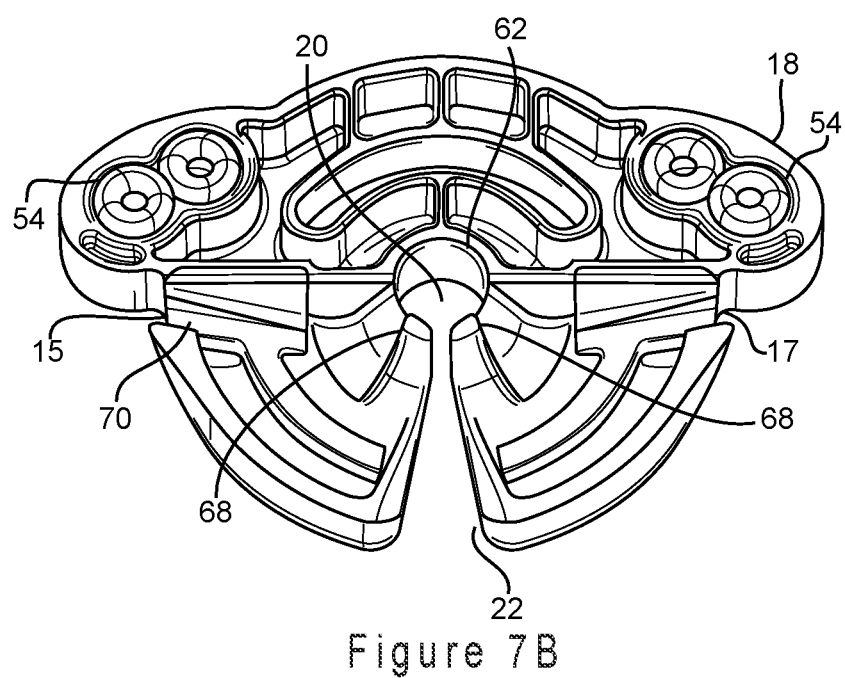

FIG. 7B shows a perspective view of an interior surface of the top section 18 of the wire lock assembly 10. In this embodiment, the interior surface of the top section of the medical device may include moldings that pair with features of the intermediate section. The notch is in fluid communication with the top opening of the top section of the medical device. A pair of O-rings 54 is positioned proximate to each wire guide tail lock disposed within the interior surface of the top section. Wire guide locking slots 15, 17, created by removing material from the top section 18 of the wire lock assembly 10, are positioned on opposite ends of the wire lock assembly 10. The wire guide locking slots 15, 17 are defined by the top portion of the wire lock assembly 10 and extend from the top opening 62 to the outer edges of the top portion 18 of the wire lock assembly 10. Each wire guide locking slot 15 and 17 include a securing mechanism, such as a snap-fit locking mechanism 68, that further facilitates a locking of the wire guide. The interior surface of the top section 18 may further include an overmold material 70 positioned in areas adjoining the wire guide locking slots 15, 17, which may allow for increased ease-of-use and wire guide security. The overmold material 70 may be manufactures from suitable elastic materials. In a preferred embodiment, the overmold material 70 may comprise a thermoplastic elastic material. In alternative embodiments, the top portion 18 may formed without overmold material 70.

Figure 8A:
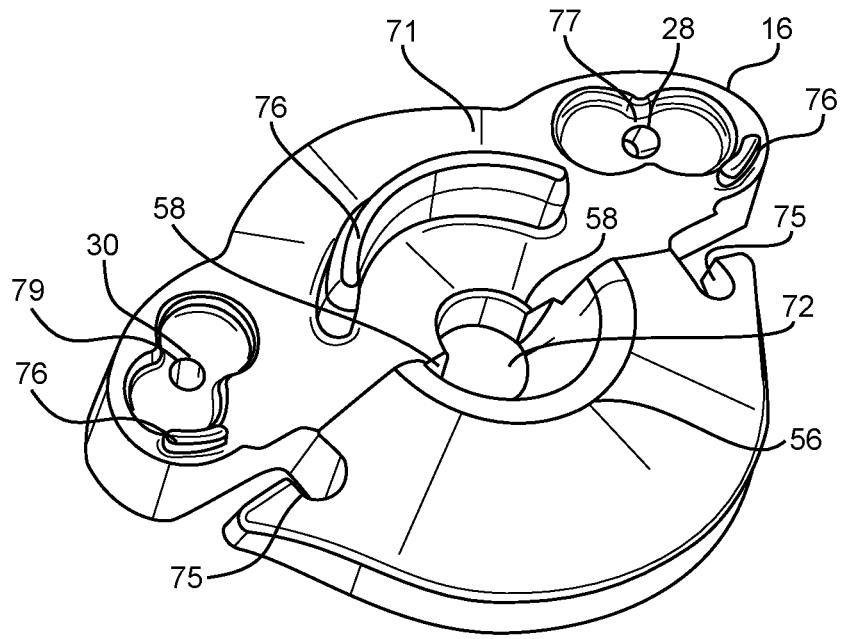
FIGS. 8A and 8B illustrate an intermediate section of an embodiment of a wire lock assembly.
Figure 8B:
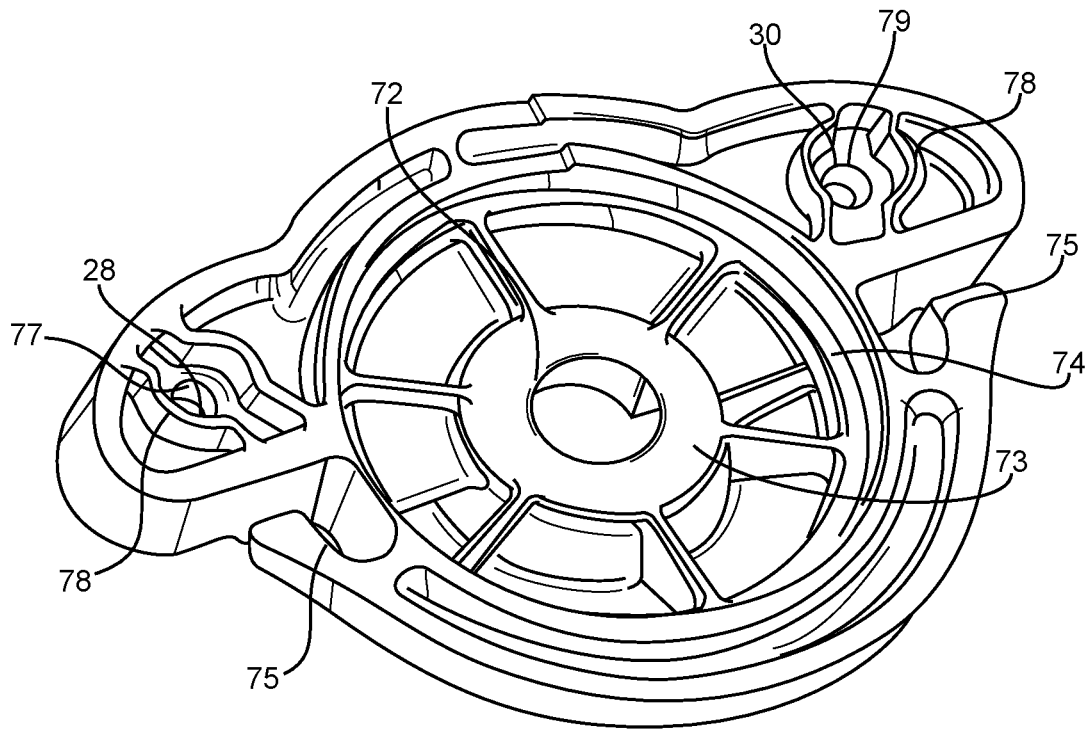

FIGS. 8A and 8B show perspective views of a top surface 71 and a bottom surface 73, respectively, of an intermediate section 16 of the wire lock assembly 10. Referring to FIG. 8A, the intermediate section 16 includes an intermediate opening 72 that is in fluid communication with both the top opening 62 of the top section 18 of the wire lock assembly in order to form the central pathway when the top section 18 and intermediate section 16 are secured together. As shown, the intermediate section 16 includes a raised, generally rounded surface 56 extending about a section of the periphery of the intermediate opening 72. The raised rounded surface 56 includes a taper and extends from the intermediate opening 72 to the edge of the intermediate section. When the intermediate section 16 is combined with the top section 18 of the wire lock assembly 10, the non-linear wire guide pathway is formed by the spacing created by the tapered, raised rounded surface 56 and the top section 18 of the wire lock assembly 10. The intermediate section 16 of the wire lock assembly 10 further includes a flattened edge 58 positioned adjacent to the intermediate opening 72. The intermediate section 16 further includes a cavity 75 on opposing sides for receiving a wire guide when the wire guide is positioned in the wire guide locking tail locks. Openings 77, 79 for wire guide tail locks 28, 30 are disposed through the intermediate section 16 and are positioned on opposite sides. Molded elements 76 are positioned on opposite sides of the top surface 71 of the intermediate section 16. The molded elements 76 are configured to engage with matching elements on the top section 18 of the wire lock assembly 10. Referring now to FIG. 8B, the bottom section 73 of the intermediate section 16 includes a well 74 for accommodating the seal 40. Molded elements 78 are positioned on opposite sides of the bottom surface 73 of the intermediate section 16. The molded elements 78 are configured to engage with matching elements on the bottom section 14 of the wire lock assembly 10.

Figure 9A:
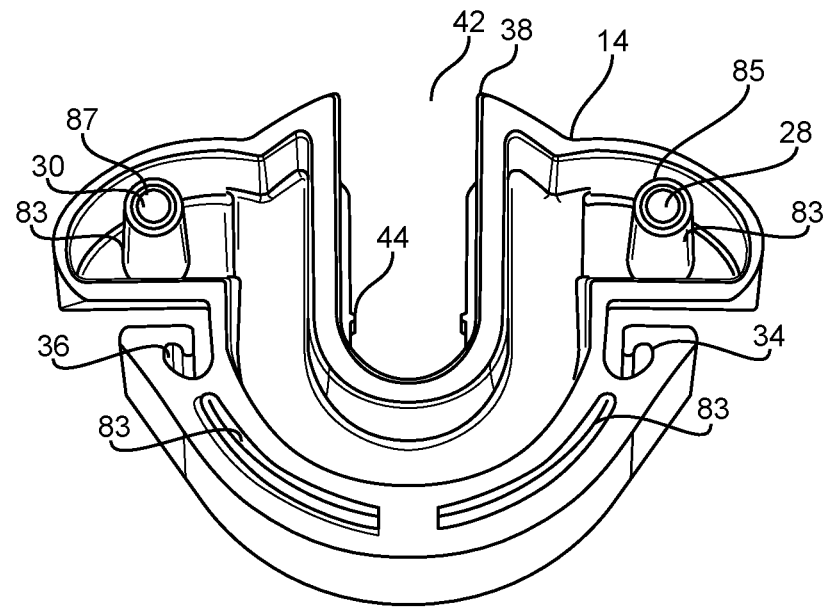
FIGS. 9A and 9B illustrate a bottom section of an embodiment of a wire lock assembly.
Figure 9B:
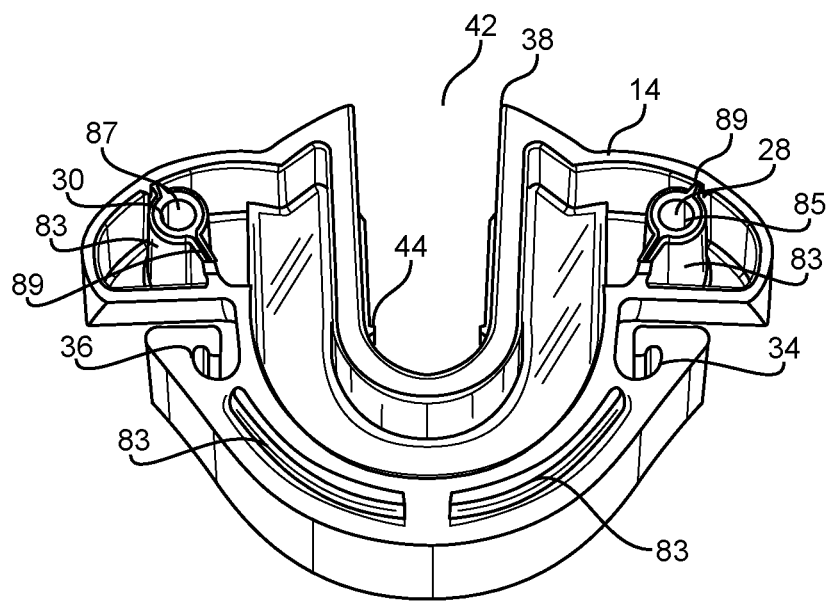

FIGS. 9A and 9B illustrate embodiments of an interior surface 81 of a bottom section 14 of the wire lock assembly. As shown in FIG. 9A, two secondary wire guide locks 34, 36 are disposed on opposite sides of the wire lock assembly 10. The secondary wire guide locks 34, 36 comprise clamps having a generally c-shaped design. An attachment mechanism 38 having a groove 42 includes a groove 42 formed through the bottom section 14 of the wire lock assembly 10. A snap-fit locking mechanism 44 is provided within the groove 42 of the attachment mechanism 38 in order to provide for a more secure fit between the wire lock assembly and a port of the second medical device. In this embodiment, the interior surface of the bottom section 14 of the wire lock assembly 10 includes moldings 83 that pair with features of the bottom surface 73 of the intermediate section 16. Openings 85, 87 for wire guide tail locks 28, 30 are disposed through the intermediate section 16 and are positioned on opposite sides. In alternative embodiments, the moldings may include gussets 89, or other reinforcements, as shown in FIG. 9B.

Figure 10:
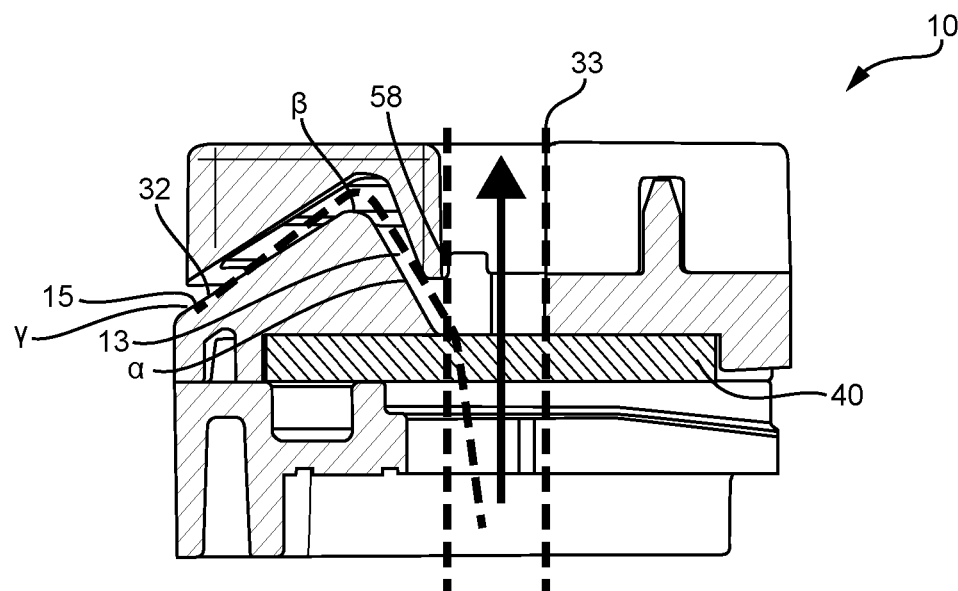
FIG. 10 illustrates a cross section of an embodiment of a wire lock assembly where a wire guide is placed in a locked position during use.

FIG. 10 shows a cross section of an embodiment of the wire lock assembly 10 where a wire guide 32 is placed in a locked position within the wire locking slot 15. As shown, a catheter 33 is being exchanged and removed while maintaining the wire guide 32 in its position within a patient. When the wire lock assembly 10 is attached to a second medical device, a wire guide 32 extending through the working channel of the second medical device would extend out through the seal 40 and the central pathway 20 of the wire lock assembly 10. While in this position, the wire guide 32 can be positioned within the wire guide locking slot 15. The non-linear wire guide locking path 13 induces a three point bend at areas $\alpha$, $\beta$, and $\gamma$ to the wire guide 32. Upon placement within the wire guide locking slot 15, the wire guide 32 is automatically placed in a locked position. This positioning is due to the stiffness or resistance to bending of a typical wire guide 32 results in a lateral force that is applied throughout the wire guide locking slot 15. This lateral force generates a frictional force between the wire guide 32 and the wire guide locking slot 15 that is sufficient to inhibit, limit, or to some extent prevent the longitudinal movement of the wire guide. However, the wire guide 32 is not damaged by the wire guide locking slot 15 since the wire guide is not pinched between opposing surfaces of the wire lock assembly 10, and because the lateral forces applied to the wire guide are spread across several locations. In particular, this configuration avoids damage to the wire guide, such as stripping, which can result from locking it within a v-shaped slot. The wire guide 32 is further secured internally by utilizing a snap-fit locking mechanism 68, as shown in FIG. 7B, which forces the wire guide 32 to want to return to a particular configuration due to the characteristics of the wire guide. The flattened edge 58 serves as a wedge between the wire guide 32 and the catheter 33 when the user pulls in the direction of the arrow on the catheter 33 in order to perform a catheter exchange. Accordingly, upon removal from the wire guide locking slot 15, a second catheter may be inserted into the patient over the wire guide 32

Figure 11:
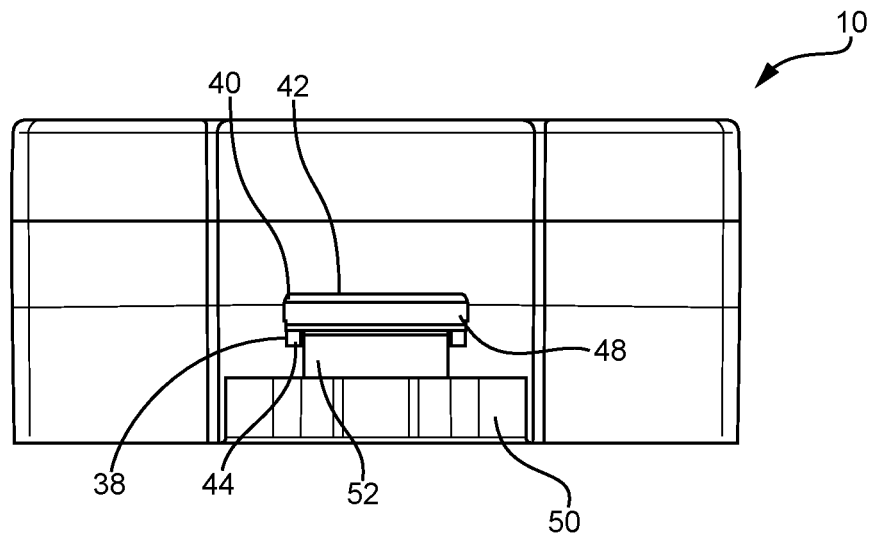
FIG. 11 illustrates an embodiment of a wire lock assembly attached to an access port.

FIG. 11 illustrates a back view of an embodiment of a wire lock assembly 10 in a fixed position on an access port 48 within the groove 42 of the attachment mechanism 38 of the wire lock assembly 10. The snap-fit locking mechanism 44 situated within the groove 42 of the attachment mechanism 38 engages the stem 52 of the access port 48 in an area adjacent to the base. In addition, the snap-fit locking mechanism 44 provides an audible sound to inform the user that the wire lock assembly 10 is attached securely to the access port 48. In this fixed position, the ramp 60 forces the stem 52 of the access port 48 into close proximity with the seal 40 such that the clearance is less than the height of an upper portion of the stem 52. Accordingly, a compressible seal is formed between when the wire lock assembly 10, the seal 40, and a wire guide and/or catheter is positioned within the central pathway 20 of the wire lock assembly 10. The depth and dimensions of the ledge 46 of the wire lock assembly 10 is sized to accommodate the base 50 of the access port 48. Similarly, the depth and dimensions of the attachment mechanism 38 are sized to accommodate the stem 50 of the access port 48.

Figure 12:
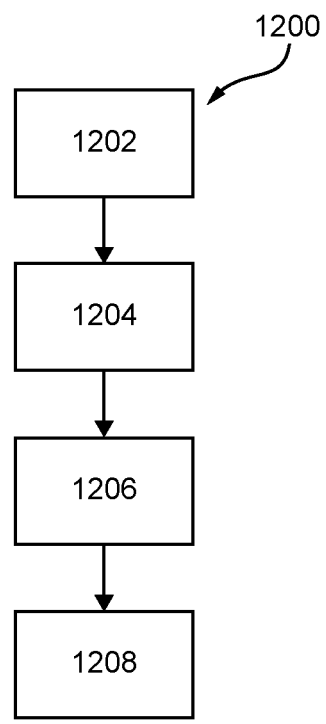
FIG. 12 illustrates an embodiment of a method of using an embodiment of the wire lock assembly.

FIG. 12 illustrates a flow chart 1200 of method steps for use of an exemplary wire lock assembly in endoscopic procedures, particularly a cannulation followed by a sphincterotomy. In this particular exemplary method, the use of an intraductal exchange biliary cannulation catheter, an intraductal exchange sphincterotome catheter, and an intraductal exchange length wire guide is described. Nevertheless, it should be understood that a variety of elongate members (e.g., wire guides and catheters, among others) can be used with the exemplary wire guide holder. This includes elongate members for biliary or non-biliary applications. Indeed, the exemplary wire guide holder can be used in conjunction with a variety of systems, including rapid exchange, monorail, or over-the-wire, peel away and/or non-peel away systems.

A physician can perform an intraducatal exchange as follows. Initially, in step 1202, a physician can prepare an intraductal exchange biliary cannulation catheter by advancing the distal end of a wire guide into the intraducatal exchange port and out of the distal end port of the catheter. Step 1204 involves inserting the wire guide and catheter through a seal in the wire guide holder, through the access port of the endoscope, and into the endoscope working channel. After readying the wire guide and cannulation catheter to cannulate the papilla of vater, the papilla is cannulated in step 1206. After cannulation, the wire guide and cannulating catheter are advanced into the bile duct. At this point, step 1208 is performed by securing one of the wire guide and the catheter in the wire guide holder. For example, the wire guide can be positioned within the wire guide locking path, as shown in FIG. 10. In this position, the non-linear wire guide locking path induces a three point bend to the wire guide wherein the wire guide is automatically placed in a locked position. At this point, advancing the catheter relative to the wire guide disconnects the wire guide and catheter. Once the wire guide and catheter are disconnected, since the wire guide is secured within the wire guide locking path, the physician can continue to use the catheter without inadvertently moving the wire guide and losing access to the target anatomy. Additionally, the proximal end of the locked wire guide may be positioned into one of the wire guide docking slots so that it is not in the physician's way. The secondary wire guide lock provides some additional securement of the wire guide. However, the wire guide is fully locked once positioned within the wire guide locking path. Upon tear down of the catheter, the flattened edge of the top portion of the medical device acts as a wedge as the catheter is being pulled.

Figure 13:
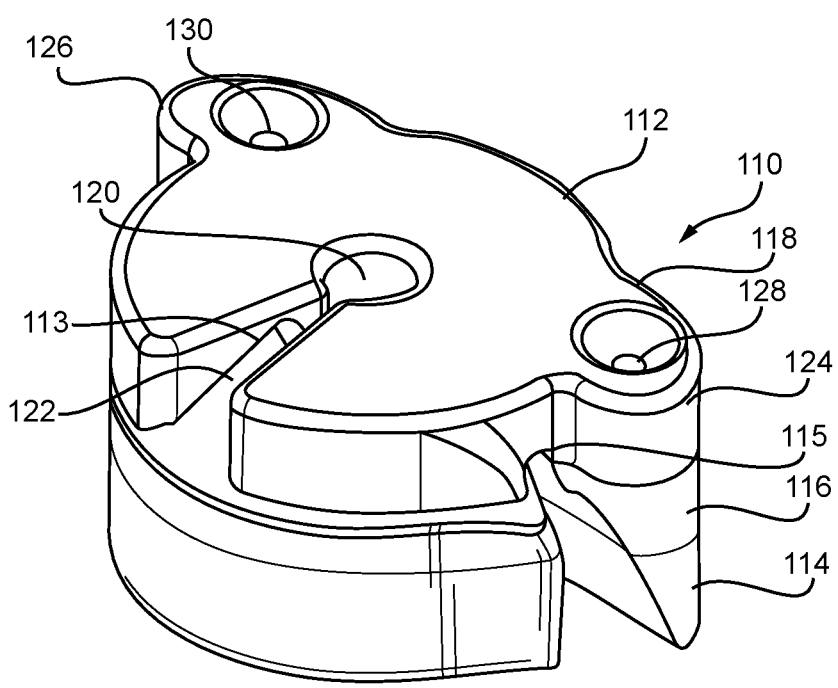
FIG. 13 illustrates a front perspective view an embodiment of a wire lock assembly.

FIG. 13 illustrates an alternate embodiment of a wire lock assembly 110. In this embodiment, the wire lock assembly 110 comprises a body 112 having a generally hemispherical shape. The body 112 of the wire lock assembly 110 may be molded to a particular form, where the wire lock assembly has a bottom section 114, intermediate section 116, and a top section 118. However, in alternative embodiments, the body 112 of the wire lock assembly 110 may comprise other geometric structures. As shown in this embodiment, a central passageway 120 is disposed through the body 112 of the wire lock assembly 10, defining a pathway for a wire guide, catheter, or similar type of elongate medical device (hereinafter collectively referred to as a "wire guide"). Within the body 112 of the wire lock assembly is a non-linear wire guide locking pathway 113 leading to a wire guide locking slot 115 for a wire guide. When the wire lock assembly 110 is attached to a medical device, such as an endo scope, a wire guide extending through the working channel of the medical device may also extend through the central passageway 120. In this position, a wire guide can be placed in the non-linear wire guide locking pathway. The body 112 of the wire lock assembly 110 includes a notch 122 disposed through the top section 118 of the body 112. The notch 122 helps to facilitate the positioning of the wire guide in the non-linear wire guide locking pathway formed within the body 112 of the wire lock assembly 110. In an exemplary embodiment, the non-linear pathway 113 and wire guide locking slot 115 induces a three point bend to the wire guide wherein the wire guide is automatically placed in a locked position. As will be discussed below, the configuration of the non-linear wire guide locking track prevents the wire guide from being damaged, as the wire guide is not pinched between opposing surface of the wire guide locking path. Further, after traversing the wire guide locking pathway 113 and is positioned within the wire guide locking slot 115, the wire guide is in an automatically locked position.

The body 112 of the wire lock assembly 110 further includes two side wings 124, 126 comprising wire guide tail locks 128, 130. The side wings 128, 130 enable the user to have a surface to grasp in order to attach and detach the wire lock assembly 110 from the port of a medical device. As shown, the side wings 124, 126 have a generally rounded surface. However, one ordinary skill in the art would understand that other configurations may be used with the side wings. The wire guide tail locks 128, 130 are disposed through the body 112 of the wire lock assembly 10 and are positioned on opposing sides of the body 112 of the wire lock assembly 10. In some embodiments, the wire guide tail locks 128, 130 may comprise one opening or a plurality of openings. The wire guide tail locks 128, 130 enable the locked wire guide to be looped over the body 112 of the wire lock assembly 110 and locked in a downward or upward position.

Figure 14:
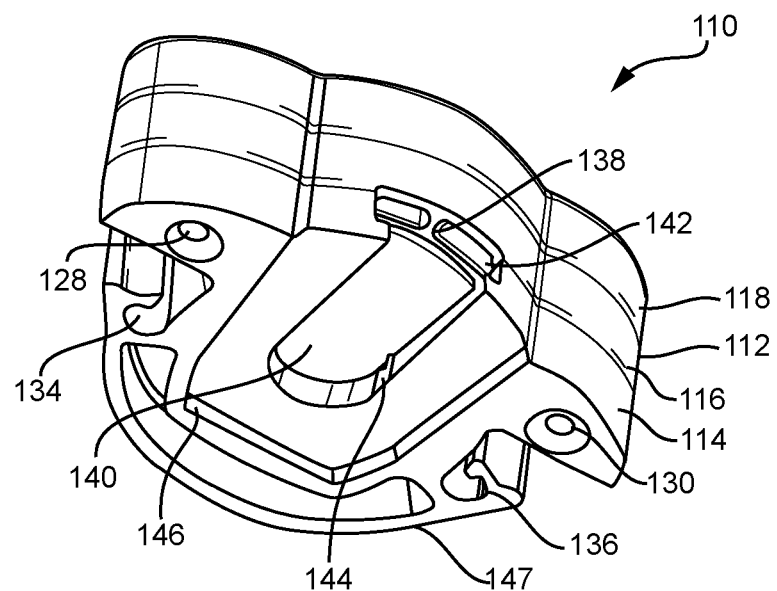
FIG. 14 illustrates a back perspective view of an embodiment of a wire lock assembly for use with a secondary medical device.

FIG. 14 illustrates a back perspective view of the wire lock assembly 110. As shown, the wire lock assembly 110 includes a central passageway 120, a pair of wire guide tail locks 128, 130 on opposing sides, a pair of secondary wire guide locks 134, 136, an attachment mechanism 138, and a seal 140 disposed within the body 112 of the wire lock assembly 110. The attachment mechanism 138 facilitates connection between the wire lock assembly 110 and a port of a second medical device. In this embodiment, the attachment mechanism 138 is configured to engage with a port of an endoscope. As shown, the attachment mechanism 138 includes a groove 142 formed through the bottom section 114 of the wire lock assembly 110. A snap-fit locking mechanism 144 is provided within the groove 142 of the attachment mechanism 138 in order to provide for a more secure fit between the medical device and the port of the second medical device. A ledge 146, having a thickness with respect to the body 112 of the wire lock assembly 110, is positioned beneath the attachment mechanism 138. In this embodiment, the ledge 146 has a semi-hemispherical configuration and includes edges 147 which expand beyond the outer perimeter of the groove 142 of the attachment mechanism 138. The ledge 146 helps to prevent unwanted rotation of the wire lock assembly 110 relative to a housing of the second medical device. The dimensions of the attachment mechanism 138 and the ledge 146 may be modified based on the dimensions of the second medical device.

The seal 140 is fluidly engaged with the central passageway 120 of the wire lock assembly 110 and is configured to limit the escape of any fluids that may be present within a working channel of a second medical device without inhibiting the insertion or movement of wire guides, catheters, or similar elongate devices. This configuration can be of particular benefit in preventing bodily fluids such as bile and blood from escaping and contaminating the physician and the working environment. The design and configuration of the seal 40, including the types of materials from which it may be manufactured, are well known to those skilled in the art. In this embodiment, the seal 140 is positioned between the bottom portion 114 and the intermediate portion 116 of the wire lock assembly 110. While an exemplary seal 140 may include a single slit, other types of slits, torn holes, arranged slits, or penetrable seals may alternatively be used. For example, other seal configurations include duckbill, membrane with slit (e.g., polystyrene, silicone, or another compliant polymer material), or other designs having the ability to seal around the catheter and wire guide to prevent any proximally migrating fluid from exiting the channel. The seal 40 in this embodiment is comprised of two generally flat surfaces.

Two wire guide tail locks 134, 136 are located proximate to the wire guide tail locks 128, 130 of the wire lock assembly 110 and disposed on the bottom section 114 of the wire lock assembly 110. As shown, the secondary wire guide locks 134, 136 comprise clamps having a generally c-shaped design. In alternative embodiments, other configurations may be suitable. In use, when the wire guide is locked in an outward position within the wire guide locking slot, a proximal portion of the wire guide may be placed within one of the secondary wire guide locks 134, 136 in a direction away from the user. The positioning of a proximal portion of the wire guide within one of the secondary wire guide locks 134, 136 provides a secondary lock for the wire guide, as the wire guide is placed into a locked position automatically upon being positioned within the wire guide locking slot 115.

Figure 15:
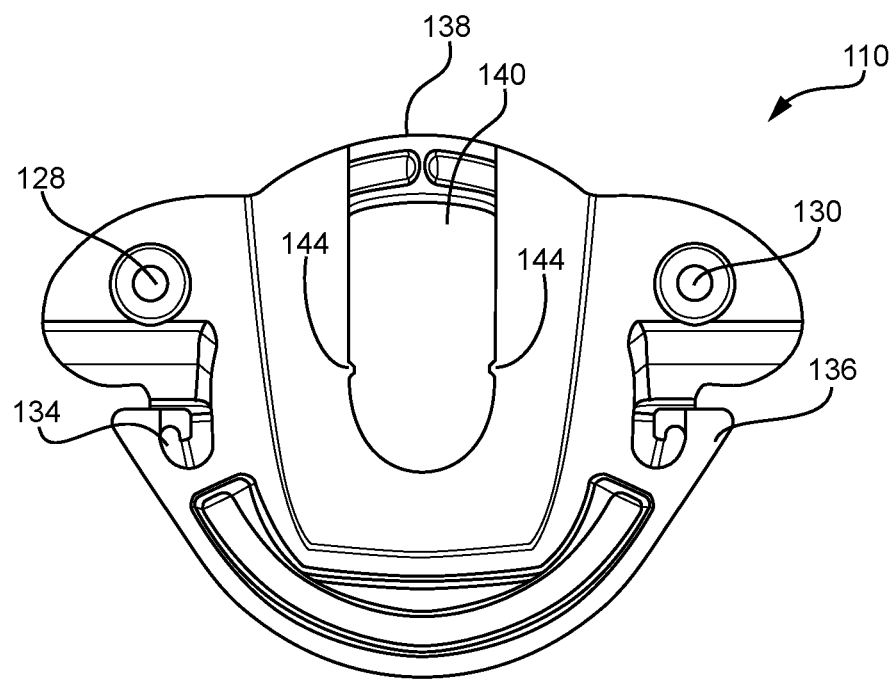
FIG. 15 illustrates a bottom view of an embodiment of a biopsy cap for use with a secondary medical device.

FIG. 15 illustrates a bottom view of the wire guide lock assembly 110. As shown, the wire guide locking assembly 110 includes a pair of tail locks 128, 130 on opposing sides, a pair of secondary wire guide locks 134, 136, an attachment mechanism 138, and a seal 140 disposed within the body 112 of the wire lock assembly 110. A snap-fit locking mechanism 144 is provided within the groove 142 of the attachment mechanism 138 in order to provide for a more secure fit between the medical device and the port of the second medical device. A ledge 146, having a thickness with respect to the body 112 of the wire lock assembly 110, is positioned beneath the attachment mechanism 138. The seal 140 is configured to limit the escape of any fluids that may be present within a working channel of the second medical device without inhibiting the insertion or movement of wire guides, catheters, or similar elongate devices.

Figure 16:
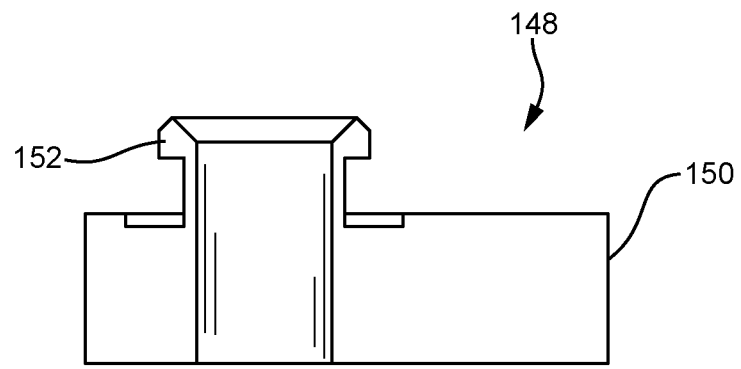
FIG. 16 illustrates an embodiment of an access port.

FIG. 16 illustrates a cross-section of an exemplary access port 148 of an endoscope. The access port 148 provides access to a working channel (not shown) that extends distally through the interior of the endoscope. The metal insert 148 may be covered by an access port cover, which may be removed to access the access port in the metal insert. The access port 148 comprises of a base 150 and a stem 152 having a height and width. In some embodiments, the access port 148 has a generally t-shaped configuration. One of skill will understand that ports having other types of configuration may also be used.

Figure 17:
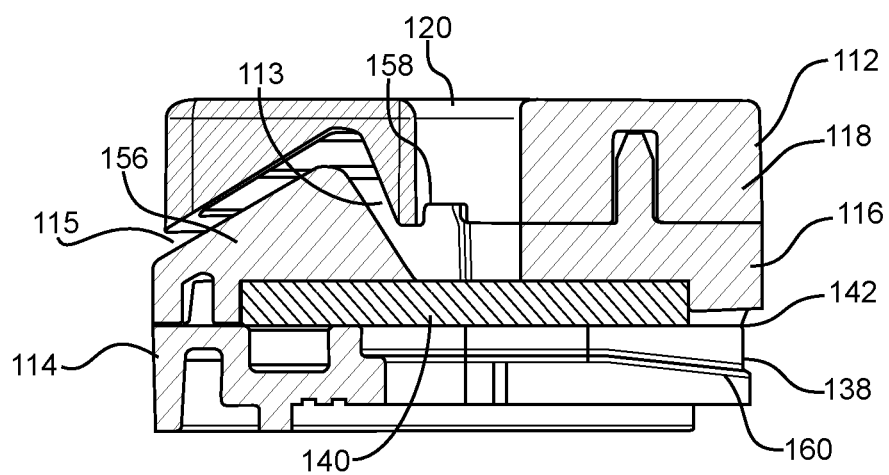
FIG. 17 illustrates a cross-sectional view an embodiment of a wire lock assembly for use with a secondary medical device.

FIG. 17 illustrates a cross-sectional view of the wire lock assembly 110. The top portion 118 and the intermediate portion 116 of the wire lock assembly form a wire guide locking path 113 leading to the wire locking slot 113. The wire guide locking path 113 includes a raised surface 156 that is positioned on the intermediate section of the wire lock assembly. The raised rounded surface 156 extends about the periphery of the central pathway 120 and has a generally semi-hemispherical shape. As shown, the raised rounded surface includes a taper extending from central pathway 120 to the outer periphery of the intermediate section 116. The tapered section of the raised rounded surface 156 increases in diameter as it expands toward the outer periphery of the intermediate section 116. The raised rounded surface 156 includes a tapered, generally rounded surface that extends about the periphery of the intermediate opening. The wire lock assembly 110 further includes a flattened edge 158 positioned on the intermediate section 116 of the wire lock assembly. When the wire guide is secured in the wire guide locking slot, the flattened edge may be used as a wedge between the wire guide and the catheter when the user pulls upward on the catheter in order to perform a catheter exchange. Within the groove 142 of the attachment mechanism 138 of the wire lock assembly 10 is an angled ramp 160. The angled ramp 160 allows the wire lock assembly 10 to be secured to a second medical device by sliding the wire lock assembly 110 onto a port of the second medical device.

Figure 18:
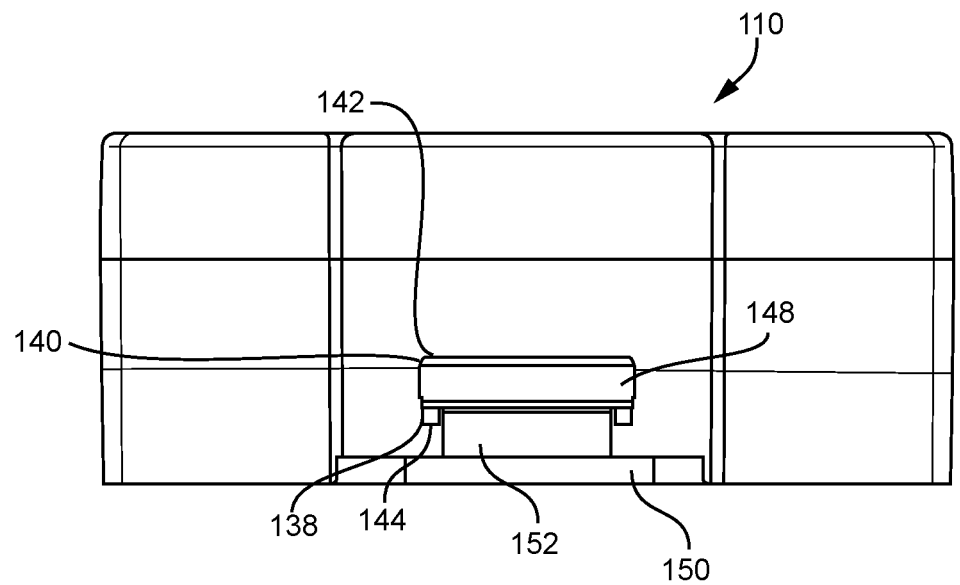
FIG. 18 illustrates an embodiment of a wire lock assembly attached to an access port.

FIG. 18 illustrates a back view of an embodiment of a wire lock assembly 110 in a fixed position on an access port 148 within the groove 142 of the attachment mechanism 138 of the wire lock assembly 110. The snap-fit locking mechanism 144 situated within the groove 142 of the attachment mechanism 138 engages the stem 152 of the access port 148 in an area adjacent to the base. In addition, the snap-fit locking mechanism 144 provides an audible sound to inform the user that the wire lock assembly 110 is attached securely to the access port 148. In this fixed position, the ramp 160 forces the stem 152 of the access port 148 into close proximity with the seal 140 such that the clearance is less than the height of an upper portion of the stem 152. Accordingly, a compressible seal is formed between when the wire lock assembly 110 and a wire guide and/or catheter is positioned within the central pathway 120 of the wire lock assembly 110. The depth and dimensions of the ledge 146 of the wire lock assembly 110 is sized to accommodate the base 150 of the access port 148. Similarly, the depth and dimensions of the attachment mechanism 138 are sized to accommodate the stem 150 of the access port 148.

Figure 19:
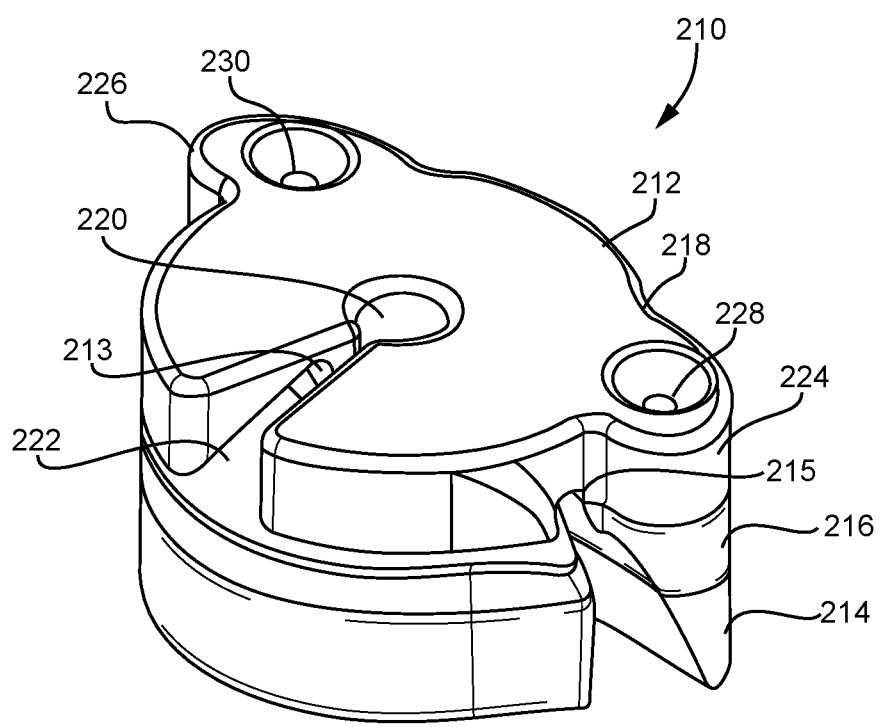
FIG. 19 illustrates a front perspective view an embodiment of a wire lock assembly.

FIG. 19 illustrates an alternate embodiment of a wire lock assembly 210. In this embodiment, the wire lock assembly 210 comprises a body 212 having a generally hemispherical shape. The body 212 of the wire lock assembly 210 may be molded to a particular form, where the wire lock assembly has a bottom section 214, intermediate section 216, and a top section 218. However, in alternative embodiments, the body 212 of the wire lock assembly 210 may comprise other geometric structures. As shown in this embodiment, a central pathway 220 is disposed through the body 212 of the wire lock assembly 210, defining a pathway for a wire guide, catheter, or similar type of elongate medical device (hereinafter collectively referred to as a "wire guide"). Within the body 212 of the wire lock assembly is a non-linear wire guide locking pathway 213 leading to a wire guide locking slot 215 for a wire guide. When the wire lock assembly 210 is attached to a medical device, such as an endoscope, a wire guide extending through the working channel of the medical device may also extend through the central pathway 220. In this position, a wire guide can be placed in the non-linear wire guide locking pathway. The body 212 of the wire lock assembly 210 includes a notch 222 disposed through the top section 218 of the body 212. The notch 222 helps to facilitate the positioning of the wire guide in the non-linear wire guide locking pathway formed within the body 212 of the wire lock assembly 210. In an exemplary embodiment, the non-linear pathway 213 and wire guide locking slot 215 induces a three point bend to the wire guide wherein the wire guide is automatically placed in a locked position. As will be discussed below, the configuration of the non-linear wire guide locking track prevents the wire guide from being damaged, as the wire guide is not pinched between opposing surface of the wire guide locking path. Further, after traversing the wire guide locking pathway 213 and is positioned within the wire guide locking slot 215, the wire guide is in an automatically locked position.

The body 212 of the wire lock assembly 10 further includes two side wings 224, 226 comprising wire guide tail locks 228, 230. The side wings 228, 230 enable the user to have a surface to grasp in order to attach and detach the wire lock assembly 10 from the port of a medical device. As shown, the side wings 224, 226 have a generally rounded surface. However, one ordinary skill in the art would understand that other configurations may be used with the side wings. The wire guide tail locks 228, 230 are disposed through the body 212 of the wire lock assembly 210 and are positioned on opposing sides of the body 212 of the wire lock assembly 210. In some embodiments, the wire guide tail locks 228, 230 may comprise one opening or a plurality of openings. The wire guide tail locks 228, 230 enable the locked wire guide to be looped over the body 212 of the wire lock assembly 10 and locked in a downward or upward position.

Figure 20:
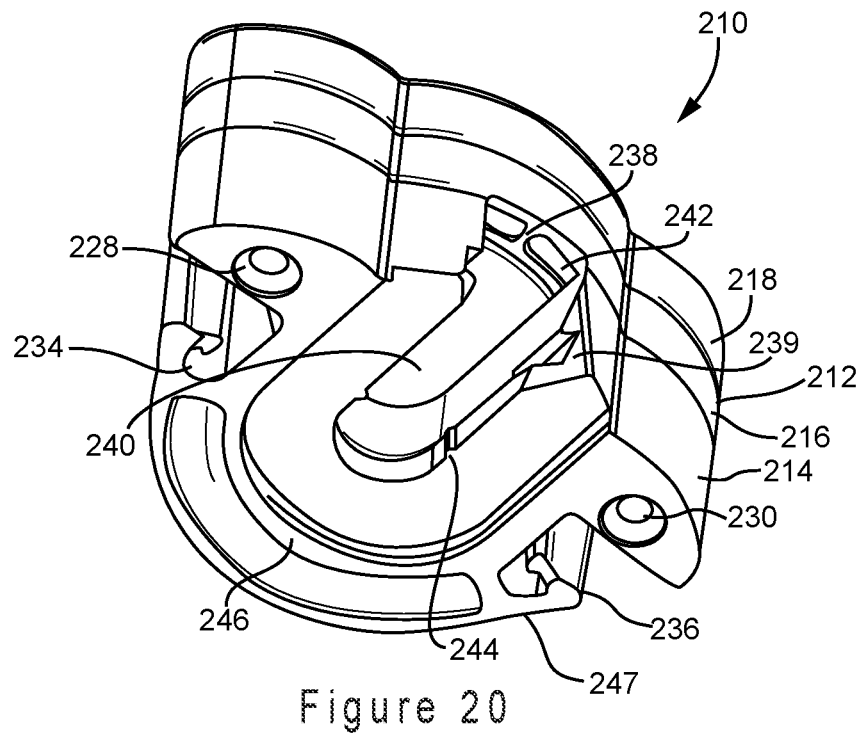
FIG. 20 illustrates a back perspective view of an embodiment of a wire lock assembly for use with a secondary medical device.

FIG. 20 illustrates a back perspective view of the wire lock assembly 210. As shown, the wire lock assembly 210 includes a central pathway 220, a pair of wire guide locks 228, 230 on opposing sides, a pair of secondary wire guide locks 234, 236, an attachment mechanism 238, and a seal 240 disposed within the body 212 of the wire lock assembly 210. The attachment mechanism 238 facilitates connection between the wire lock assembly 210 and a port of a second medical device. In this embodiment, the attachment mechanism 238 is configured to engage with a port of an endoscope. As shown, the attachment mechanism 238 includes a groove 242 formed through the bottom section 214 of the wire lock assembly 210. A snap-fit locking mechanism 244 is provided within the groove 242 of the attachment mechanism 238 in order to provide for a more secure fit between the medical device and the port of the second medical device. A ledge 246, having a thickness with respect to the body 212 of the wire lock assembly 210, is positioned beneath the attachment mechanism 238. In this embodiment, the ledge 246 has a semi-hemispherical configuration and includes edges 248 which expand beyond the outer perimeter of the groove 242 of the attachment mechanism 238. The ledge 246 helps to prevent unwanted rotation of the wire lock assembly relative to a housing of the second medical device. The dimensions of the attachment mechanism 238 and the ledge 246 may be modified based on the dimensions of the second medical device. As shown in this embodiment, the attachment mechanism is configured to accommodate the size of a stem and base of a port having greater dimensions than the embodiments of FIGS. 1-17. The attachment mechanism 238 includes an angled edge 239. The angled edge 239 may be advantageous when the wire lock assembly 210 is used on a medical device having a circular housing, as the angled edge 239 helps to inhibit rotation of the wire lock assembly 210 on the port of the medical device.

The seal 240 is fluidly engaged with the central pathway 220 of the wire lock assembly 210 and is configured to limit the escape of any fluids that may be present within a working channel of a second medical device without inhibiting the insertion or movement of wire guides, catheters, or similar elongate devices. This configuration can be of particular benefit in preventing bodily fluids such as bile and blood from escaping and contaminating the physician and the working environment. The design and configuration of the seal 240, including the types of materials from which it may be manufactured, are well known to those skilled in the art. In this embodiment, the seal 240 is positioned between the bottom portion 214 and the intermediate portion 216 of the wire lock assembly 210. While an exemplary seal 240 may include a single slit, other types of slits, torn holes, arranged slits, or penetrable seals may alternatively be used. For example, other seal configurations include duckbill, membrane with slit (e.g., polystyrene, silicone, or another compliant polymer material), or other designs having the ability to seal around the catheter and wire guide to prevent any proximally migrating fluid from exiting the channel. The seal 240 in this embodiment is comprised of two generally flat surfaces.

Two secondary wire guide locks 234, 236 are located proximate to the wire guide tail locks 228, 230 of the wire lock assembly 210 and disposed on the bottom section 214 of the wire lock assembly 210. As shown, the secondary wire guide locks 234, 236 comprise clamps having a generally c-shaped design. In alternative embodiments, other configurations may be suitable. In use, when the wire guide is locked in an outward position within the wire guide locking slot, a proximal portion of the wire guide may be placed within one of the secondary wire guide locks 234, 236 in a direction away from the user. The positioning of a proximal portion of the wire guide within one of the secondary wire guide locks 234, 236 provides a secondary lock for the wire guide, as the wire guide is placed into a locked position automatically upon being positioned within the wire guide locking slot 215.

Figure 21:
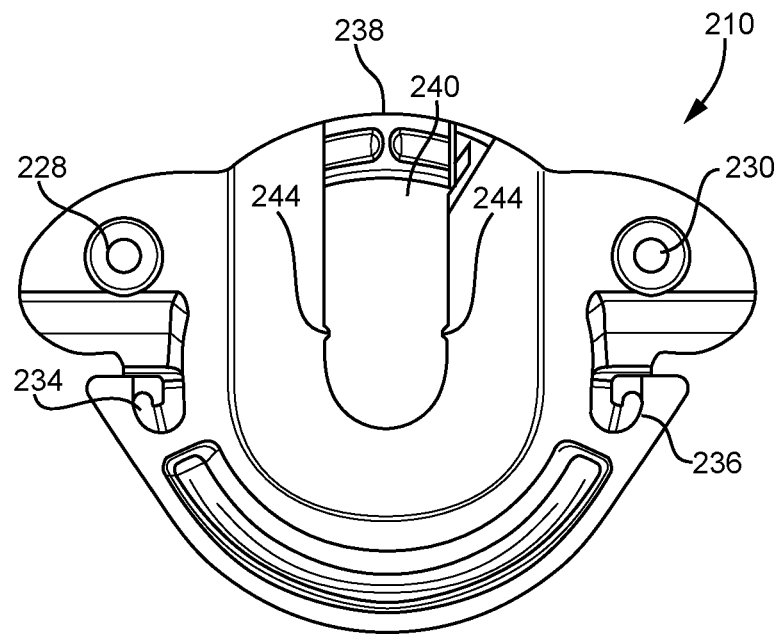
FIG. 21 illustrates a bottom view of an embodiment of a wire lock assembly for use with a secondary medical device.

FIG. 21 illustrates a bottom view of the wire lock assembly. As shown, the wire guide locking assembly 210 includes a pair of wire guide tail locks 228, 230 on opposing sides, a pair of secondary wire guide locks 234, 236, an attachment mechanism 238, and a seal 240 disposed within the body 212 of the wire lock assembly 210. A snap-fit locking mechanism 244 is provided within the groove 242 of the attachment mechanism 238 in order to provide for a more secure fit between the medical device and the port of the second medical device. A ledge 246, having a thickness with respect to the body 212 of the wire lock assembly 210, is positioned beneath the attachment mechanism 238. The seal 240 is configured to limit the escape of any fluids that may be present within a working channel of the second medical device without inhibiting the insertion or movement of wire guides, catheters, or similar elongate devices.

Figure 22:
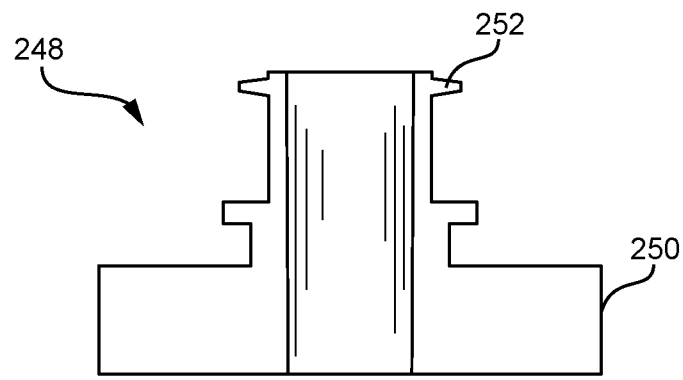
FIG. 22 illustrates an embodiment of an access port.

FIG. 22 a cross-section of an exemplary access port 248 of an endoscope. The access port 248 provides access to a working channel (not shown) that extends distally through the interior of the endoscope. The metal insert 248 may be covered by an access port cover, which may be removed to access the access port in the metal insert. The access port 248 comprises of a base 250 and a stem 252 having a height and width. In some embodiments, the access port has a generally circular configuration. One of skill will understand that ports having other types of configuration may also be used.

Figure 23:
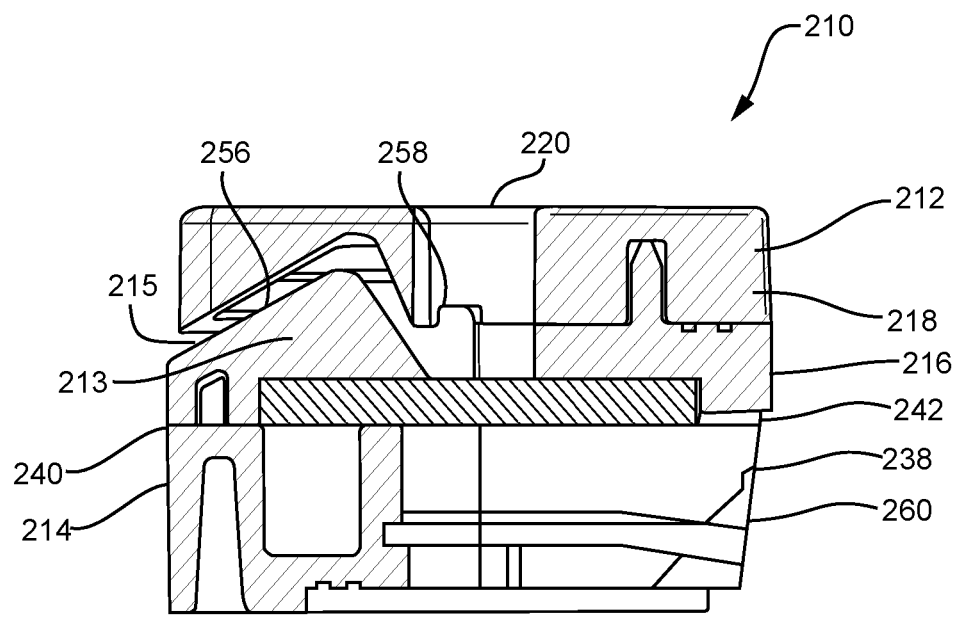
FIG. 23 illustrates a cross-sectional view an embodiment of a wire lock assembly for use with a secondary medical device.

FIG. 23 illustrates a cross-sectional view of the wire lock assembly 210. The top portion 218 and the intermediate portion 216 of the wire lock assembly form a wire guide locking path 213 leading to the wire locking slot 213. The wire guide locking path 213 includes a raised surface 256 that is positioned on the intermediate section of the wire lock assembly. The raised rounded surface 256 extends about the periphery of the central pathway 220 and has a generally semi-hemispherical shape. As shown, the raised rounded surface includes a taper extending from central pathway 220 to the outer periphery of the intermediate section 216. The tapered section of the raised rounded surface 256 increases in diameter as it expands toward the outer periphery of the intermediate section 216. The raised rounded surface 256 includes a tapered, generally rounded surface that extends about the periphery of the intermediate opening. The wire lock assembly 210 further includes a flattened edge 258 positioned on the intermediate section 216 of the wire lock assembly. When the wire guide is secured in the wire guide locking slot, the flattened edge may be used as a wedge between the wire guide and the catheter when the user pulls upward on the catheter in order to perform a catheter exchange. Within the groove 242 of the attachment mechanism 238 of the wire lock assembly 10 is an angled ramp 260. The angled ramp 260 allows the wire lock assembly 210 to be secured to a second medical device by sliding the wire lock assembly 210 onto a port of the second medical device.

Figure 24:
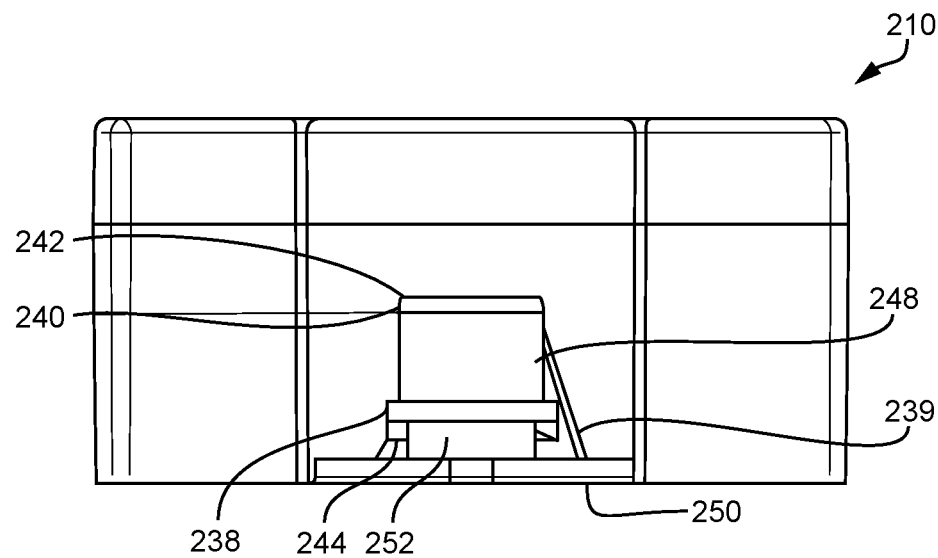
FIG. 24 illustrates an embodiment of a wire lock assembly attached to an access port.

FIG. 24 illustrates a back view of an embodiment of a wire lock assembly 210 in a fixed position on an access port 248 within the groove 242 of the attachment mechanism 238 of the wire lock assembly 210. The snap-fit locking mechanism 244 situated within the groove 242 of the attachment mechanism 238 engages the stem 252 of the access port 248 in an area adjacent to the base. In addition, the snap-fit locking mechanism 244 provides an audible sound to inform the user that the wire lock assembly 210 is attached securely to the access port 48. In this fixed position, the ramp 260 forces the stem 252 of the access port 248 into close proximity with the seal 240 such that the clearance is less than the height of an upper portion of the stem 252. Accordingly, a compressible seal is formed between when the wire lock assembly 210 and a wire guide and/or catheter is positioned within the central pathway 220 of the wire lock assembly 210. The depth and dimensions of the ledge 246 of the wire lock assembly 210 is sized to accommodate the base 250 of the access port 248. Similarly, the depth and dimensions of the attachment mechanism 238 are sized to accommodate the stem 250 of the access port 248.

Figure 25:
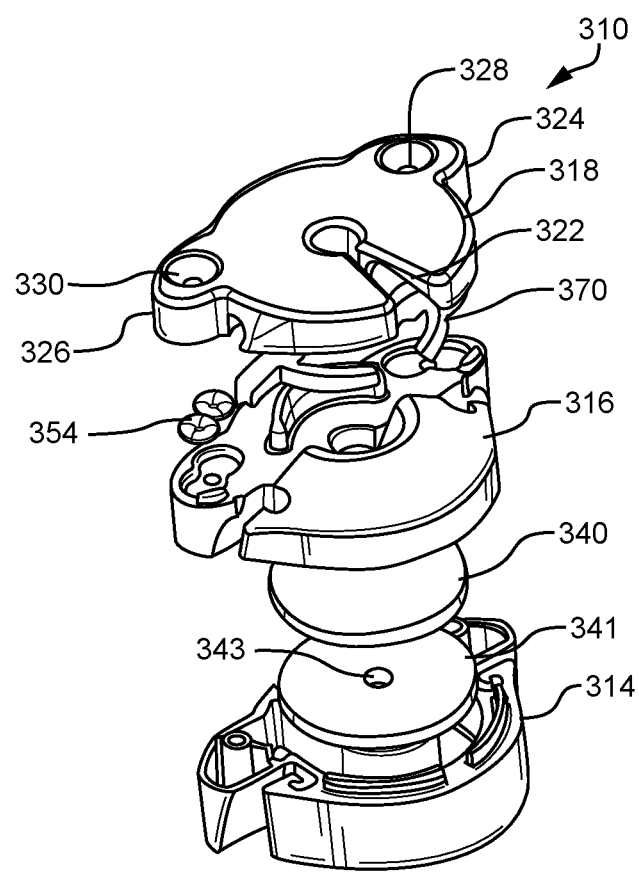
FIG. 25 illustrates an exemplary embodiment of a disassembled wire lock assembly.

FIG. 25 illustrates an exemplary alternative embodiment of a disassembled wire lock assembly. The wire lock assembly 310 having a body 312 is in three pieces formed of a suitable material such as plastic. The materials may be molded to a particular form, where the wire lock assembly 310 has a bottom section 314, intermediate section 316, and a top section 318. The body 312 of the wire lock assembly 310 further includes two side wings 324, 326 comprising wire guide tail locks 328, 330. The body 312 of the wire lock assembly 310 includes a notch 322 disposed through the top section 318 of the body 312. The notch 322 helps to facilitate the positioning of the wire guide in the non-linear wire guide locking pathway formed within the body 312 of the wire lock assembly 10. O-rings 354 are positioned in the area surrounding a wire guide tail lock 328, 330 on opposing sides of the wire lock assembly 310. The intermediate section 316 and the top section 318 may include molded regions to receive the O-rings 354 within the body of the wire lock assembly 310. The O-rings 354 provide the user some tactile feedback and friction while placing a wire guide within one of the wire guide tail locks 328, 330. In this embodiment, a pair of O-rings 354 is positioned proximate to each wire guide tail lock. In alternative embodiments, differing combinations of O-rings may be used. In further alternative embodiments, other mechanical gaskets may be used to provide tactile feedback and friction to the user. The wire lock assembly 310 may further include an overmold material 370 positioned in areas adjoining the wire guide locking slots, which may allow for increased ease-of-use and wire guide security. The overmold material 370 may be manufactures from suitable elastic materials. In a preferred embodiment, the overmold material 370 may comprise a thermoplastic elastic material. In alternative embodiments, the top portion 318 may formed without overmold material 370. Although the exemplary embodiment illustrated here is constructed by three pieces snap fit together, the wire lock assembly 310 may be made from one or more pieces that may be affixed together in any way. For example, pieces may be ultrasonically bonded, heat bonded, glued together, or affixed in any other way.

The wire assembly 310 includes a first seal 340 and a second seal 341 secured within the interior of the body of the wire lock assembly 310 between the intermediate section 316 and the bottom section 314 of the wire lock assembly 310 and in fluid communication with a central passageway 320 of the wire lock assembly 310. In this embodiment, the first seal 340 is fluidly engaged with the central passageway 320 of the wire lock assembly 310 and is configured to limit the escape of any fluids that may be present within a working channel of the second medical device without inhibiting the insertion or movement of wire guides, catheters, or similar elongate devices. This configuration can be of particular benefit in preventing bodily fluids such as bile and blood from escaping and contaminating the physician and the working environment. The design and configuration of the first seal 340, including the types of materials from which it may be manufactured, are well known to those skilled in the art. While an exemplary seal may include a single slit, other types of slits, torn holes, arranged slits, or penetrable seals may alternatively be used. For example, other seal configurations include duckbill, membrane with slit (e.g., polystyrene, silicone, or another compliant polymer material), or other designs having the ability to seal around the catheter and wire guide to prevent any proximally migrating fluid from exiting the channel. The second seal 341 of this embodiment is positioned distal to the first seal 340. The second seal 341 includes an opening 343 that is fluidly engaged with the first seal 340 and the central passageway 320 of the wire lock assembly 310. The opening 343 of the second seal 341 allows the first seal 340 to flex within the second seal 341 during use of the central passageway 320 of the wire lock assembly 310. This embodiment may be advantageous when used with ports having a nominal difference between the opening to the port and the accessory channel with the port. The dimensions of the opening 343 of the second seal 341 may be determined based on the diameter of the port for use with this embodiment of the wire lock assembly 310.

Figure 26A:
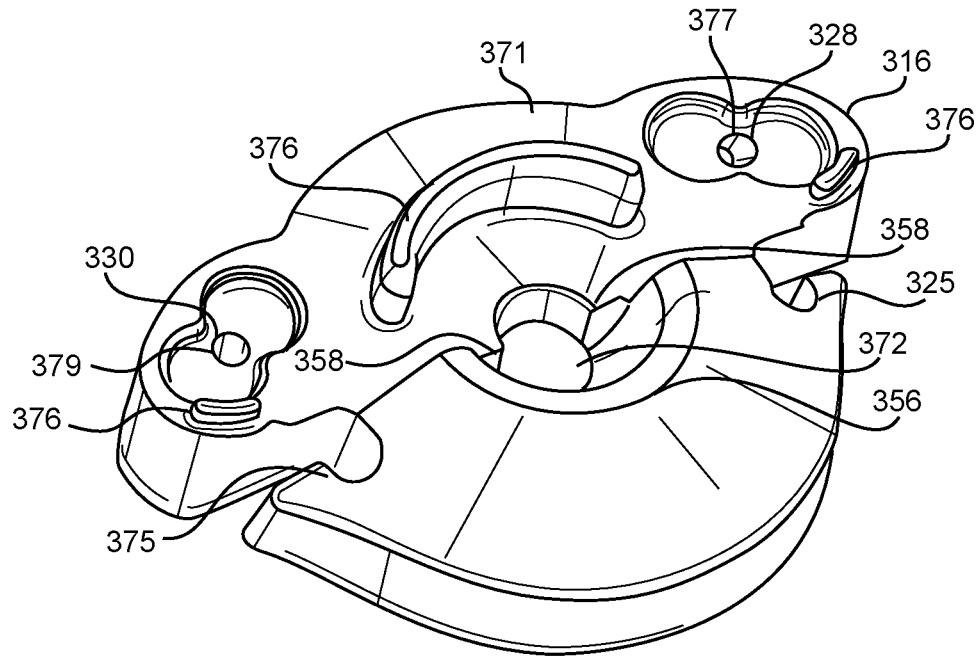
FIGS. 26A and 26B illustrate an intermediate section of an embodiment of a wire lock assembly.
Figure 26B:
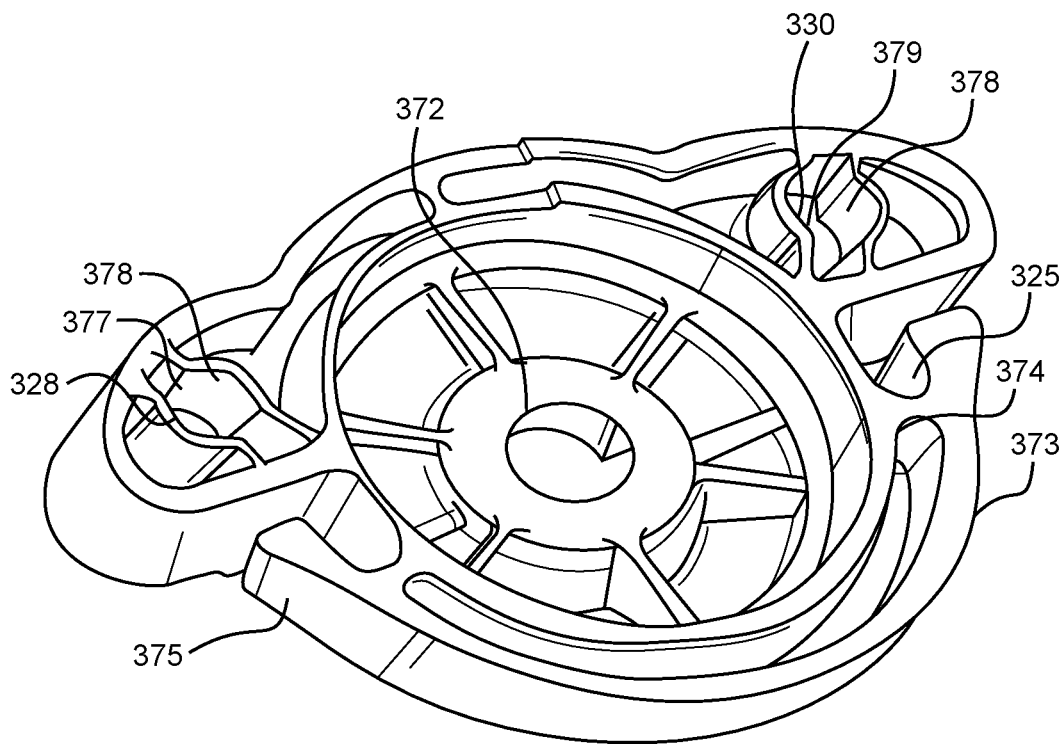

FIGS. 26A and 26B show perspective views of a top surface 371 and a bottom surface 373, respectively, of an intermediate section 316 of the wire lock assembly 310. Referring to FIG. 26A, the intermediate section 316 includes an intermediate opening 372 that is in fluid communication with both the top opening 362 of the top section 318 of the wire lock assembly in order to form the central pathway when the top section 318 and intermediate section 316 are secured together. As shown, the intermediate section 316 includes a raised, generally rounded surface 356 extending about a section of the periphery of the intermediate opening 372. The raised rounded surface 356 includes a taper and extends from the intermediate opening 372 to the edge of the intermediate section. When the intermediate section 316 is combined with the top section 318 of the wire lock assembly 310, the non-linear wire guide pathway is formed by the spacing created by the tapered, raised rounded surface 356 and the top section 318 of the wire lock assembly 10. The intermediate section 316 of the wire lock assembly 310 further includes a flattened edge 358 positioned adjacent to the intermediate opening 372. The intermediate section 16 further includes a cavity 375 on opposing sides for receiving a wire guide when the wire guide is positioned in the wire guide locking tail locks. Openings 377, 379 for wire guide tail locks 328, 330 are disposed through the intermediate section 316 and are positioned on opposite sides. Molded elements 376 are positioned on opposite sides of the top surface 371 of the intermediate section 316. The molded elements 376 are configured to engage with matching elements on the top section 318 of the wire lock assembly 310. Referring now to FIG. 8B, the bottom section 373 of the intermediate section 316 includes a well 374 for accommodating the first seal 340 and the second seal 341. Molded elements 378 are positioned on opposite sides of the bottom surface 373 of the intermediate section 316. The molded elements 378 are configured to engage with matching elements on the bottom section 314 of the wire lock assembly 310.

Figure 27:
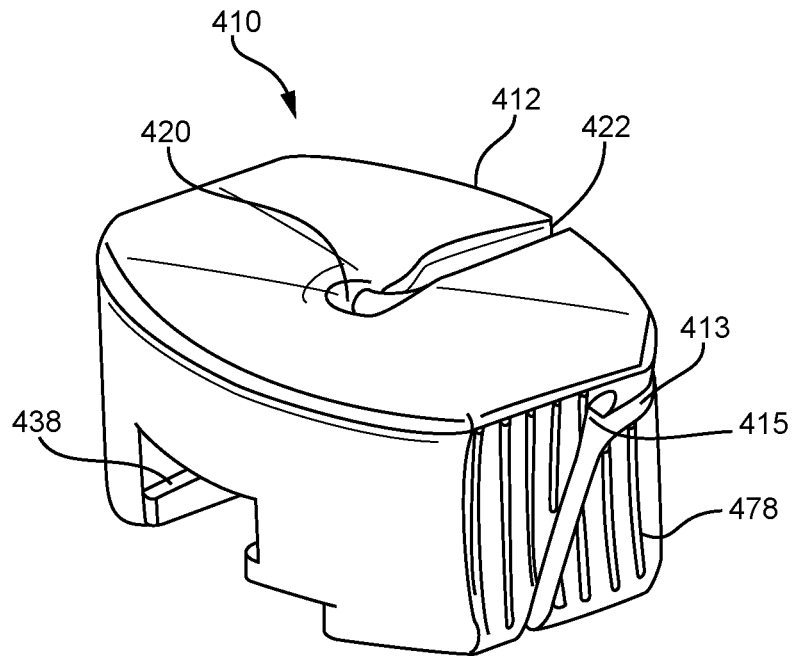
FIG. 27 illustrates an embodiment of a wire lock assembly.

FIG. 27 illustrates an alternate embodiment of a wire lock assembly 410. In this embodiment, the wire lock assembly 410 comprises a body 412 having a generally hemispherical shape. However, in alternative embodiments, the body 412 of the wire lock assembly 410 may comprise other geometric structures. As shown in this embodiment, a central pathway 420 is disposed through the body 412 of the wire lock assembly 10, defining a pathway for a wire guide, catheter, or similar type of elongate medical device (hereinafter collectively referred to as a "wire guide"). Within the body 412 of the wire lock assembly is a non-linear wire guide locking pathway 413 leading to a wire guide locking slot 415 for a wire guide. When the wire lock assembly 410 is attached to a medical device, such as an endoscope, a wire guide extending through the working channel of the medical device may also extend through the central pathway 420. In this position, a wire guide can be placed in the non-linear wire guide locking pathway. The body 412 of the wire lock assembly 410 includes a notch 422 disposed through the top section 418 of the body 412. The notch 422 helps to facilitate the positioning of the wire guide in the non-linear wire guide locking pathway formed within the body 412 of the wire lock assembly 410. In an exemplary embodiment, the non-linear pathway 413 and wire guide locking slot 415 induces a three point bend to the wire guide wherein the wire guide is automatically placed in a locked position. As will be discussed below, the configuration of the non-linear wire guide locking track prevents the wire guide from being damaged, as the wire guide is not pinched between opposing surface of the wire guide locking path. Further, after traversing the wire guide locking pathway 13 and is positioned within the wire guide locking slot 415, the wire guide is in an automatically locked position. An attachment mechanism 438 is provided and facilitates connection between the wire lock assembly 410 and a port of a second medical device. The body 412 of the wire lock assembly 410 further includes finger grooves 478 positioned on the periphery of the biopsy cap on opposite sides to ease attachment of the device to the endoscope and to provide a better grip on the biopsy cap.

Figure 28:
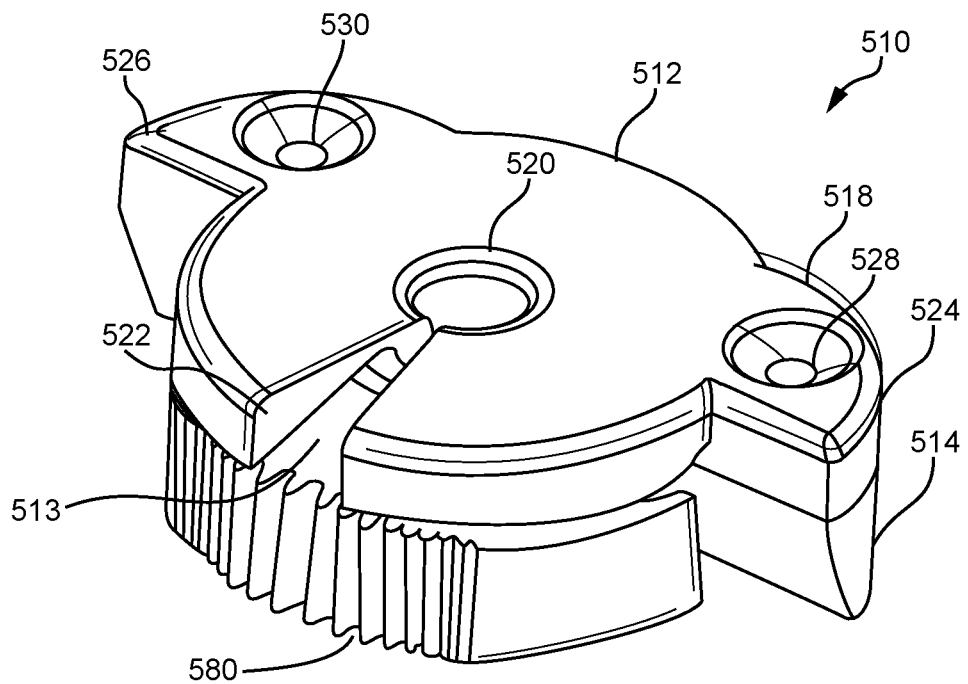
FIG. 28 illustrates an embodiment of a wire lock assembly.

FIG. 28 illustrates an embodiment of a wire lock assembly 510. In this embodiment, the wire lock assembly 510 comprises a body 512 having a generally hemispherical shape. The body 512 of the wire lock assembly 510 may be molded to a particular form, where the wire lock assembly has a bottom section 514, intermediate section 516, and a top section 518. However, in alternative embodiments, the body 512 of the wire lock assembly 510 may comprise other geometric structures. As shown in this embodiment, a central pathway 520 is disposed through the body 512 of the wire lock assembly 510, defining a pathway for a wire guide, catheter, or similar type of elongate medical device (hereinafter collectively referred to as a "wire guide"). Within the body 512 of the wire lock assembly is a non-linear wire guide locking pathway 513 leading to a wire guide locking slot 15 for a wire guide. When the wire lock assembly 510 is attached to a medical device, such as an endoscope, a wire guide extending through the working channel of the medical device may also extend through the central pathway 520. In this position, a wire guide can be placed in the non-linear wire guide locking pathway. The body 512 of the wire lock assembly 510 includes a notch 522 disposed through the top section 518 of the body 512. The notch 522 helps to facilitate the positioning of the wire guide in the non-linear wire guide locking pathway formed within the body 512 of the wire lock assembly 510. In an exemplary embodiment, the non-linear pathway 513 and wire guide locking slot 515 induces a three point bend to the wire guide wherein the wire guide is automatically placed in a locked position. As will be discussed below, the configuration of the non-linear wire guide locking track prevents the wire guide from being damaged, as the wire guide is not pinched between opposing surface of the wire guide locking path. Further, after traversing the wire guide locking pathway 513 and is positioned within the wire guide locking slot 515, the wire guide is in an automatically locked position. A flexible spine 580 is disposed on a surface of the body of the wire lock assembly 510. In one embodiment, the flexible spine 580 is positioned on the bottom surface of the device. The flexible spine 580 may provide stress relief around a port when it is positioned on a second medical device such as an endoscope.

The body 512 of the wire lock assembly 510 further includes two side wings 524, 526 comprising wire guide tail locks 528, 530. The side wings 524, 526 enable the user to have a surface to grasp in order to attach and detach the wire lock assembly 510 from the port of a medical device. As shown, the side wings 524, 526 have a generally rounded surface. However, one ordinary skill in the art would understand that other configurations may be used with the side wings. The wire guide tail locks 528, 530 are disposed through the body 512 of the wire lock assembly 510 and are positioned on opposing sides of the body 512 of the wire lock assembly 510. In some embodiments, the wire guide tail locks 528, 530 may comprise one opening or a plurality of openings. The wire guide tail locks 528, 530 enable the locked wire guide to be looped over the body 512 of the wire lock assembly 510 and locked in a downward or upward position.

Figure 29:
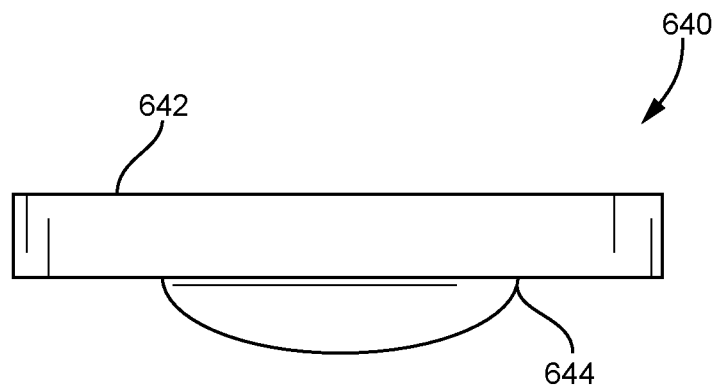
FIG. 29 illustrates an alternative embodiment of a seal for use with a wire lock assembly.

FIG. 29 illustrates an alternative embodiment of a seal 640 for use with a wire lock assembly. The seal includes a first flat surface 642 and a second surface 644 having a concave, bowl-like configuration. In this embodiment, the second surface 644 may allow for greater variance in connection points when the wire lock assembly is positioned upon a second medical device. In particular, the bowl-shaped second surface 644 will sit within an opening of a connection port of the second medical device. This configuration may also help in providing an adequate seal where the wire lock assembly is going to be positioned on multiple medical devices having varying dimensions for the connection port.

Figure 30A:
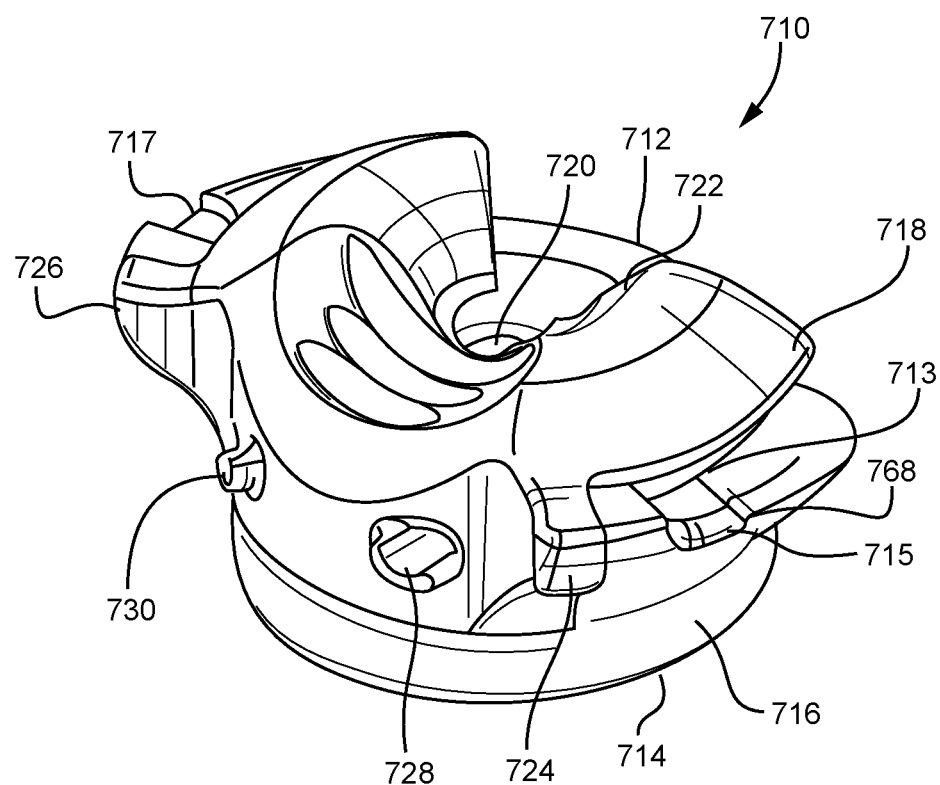
FIGS. 30A and 30B illustrate an alternative embodiment of a wire lock assembly for use with a secondary medical device.
Figure 30B:
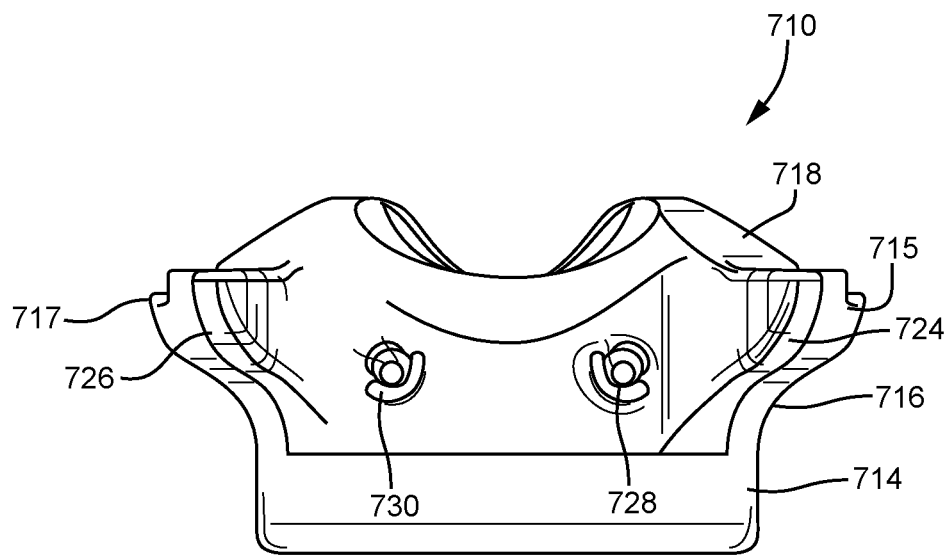

FIGS. 30A and 30B illustrate an alternative embodiment of a wire lock assembly 710. In this embodiment, the wire lock assembly 710 comprises a body 712 having a generally hemispherical shape. The body 712 of the wire lock assembly 710 may be molded to a particular form, where the wire lock assembly 710 has a bottom section 714, intermediate section 716, and a top section 718. However, in alternative embodiments, the body 712 of the wire lock assembly 710 may comprise other geometric structures. As shown in this embodiment, a central pathway 720 is disposed through the body 712 of the wire lock assembly 710, defining a pathway for a wire guide, catheter, or similar type of elongate medical device (hereinafter collectively referred to as a "wire guide"). Within the body 712 of the wire lock assembly 710 is a non-linear wire guide locking pathway 713 leading to a wire guide locking slot 715 for a wire guide. When the wire lock assembly 710 is attached to a medical device, such as an endoscope, a wire guide extending through the working channel of the medical device may also extend through the central pathway 720. In this position, a wire guide can be placed in the non-linear wire guide locking pathway 720. The body 712 of the wire lock assembly 710 includes a notch 722 disposed through the top section 718 of the body 712. The notch 722 helps to facilitate the positioning of the wire guide in the non-linear wire guide locking pathway formed within the body 712 of the wire lock assembly 710. Wire guide locking slots 715, 717 are positioned on opposite sides of the wire guide locking assembly 710. The wire guide locking slot 715, 717 include a snap-fit locking mechanism 768 that further facilitates locking of the wire guide.

The body 712 of the wire lock assembly 710 further includes two side wings 724, 726. The side wings 724, 726 enable the user to have a surface to grasp in order to attach and detach the wire lock assembly 710 from the port of a medical device. As shown, the side wings 724, 726 have a generally rounded surface. However, one ordinary skill in the art would understand that other configurations may be used with the side wings 724, 726. As shown in FIGS. 30A and 30B, a pair of wire guide tail locks 728, 730 is disposed through the intermediate section 726 of the body 712 of the wire lock assembly 710 and are positioned adjacent to one another. In some embodiments, the wire guide tail locks 728, 730 may comprise one opening or a plurality of openings. The wire guide tail locks 728, 730 enable the locked wire guide to be looped around the body 712 of the wire lock assembly 710 and locked in a position transverse to the central passageway 720.

Figure 31A:
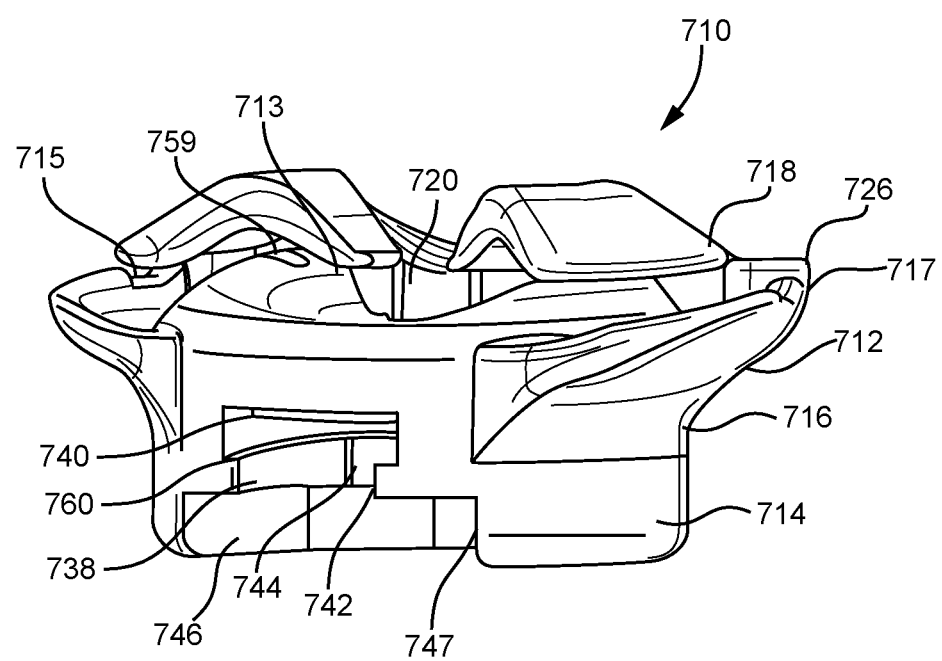
FIGS. 31A and 31B illustrates a back perspective view of an embodiment of a wire lock assembly for use with a secondary medical device.
Figure 31B:
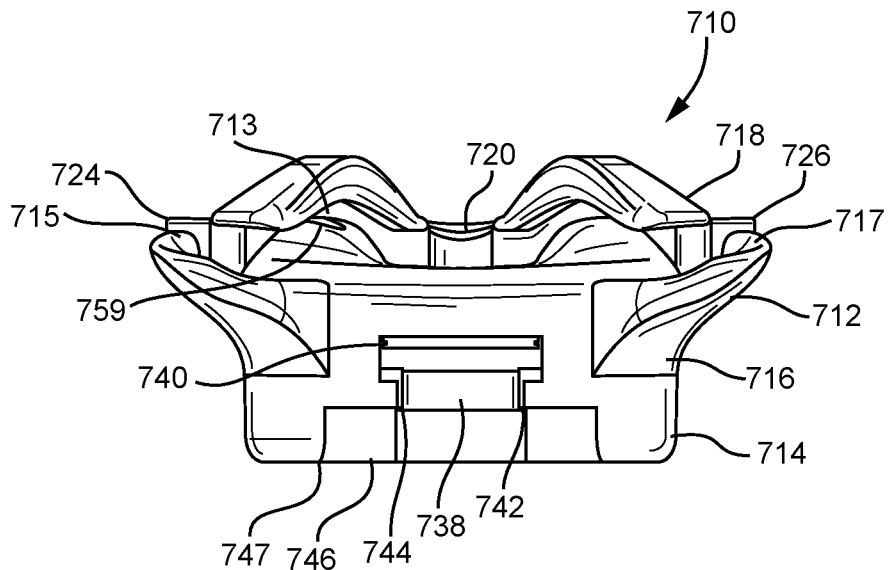

FIGS. 31A and 31B illustrate a back view of the wire guide assembly 710. As shown, the wire lock assembly 710 includes wire guide locking slots 715, 717 positioned on opposite sides of the wire guide locking assembly 710, a central pathway 720, two side wings 724, 726, an attachment mechanism 738, and a seal 740 disposed within the body 712 of the wire lock assembly 710. A non-linear wire guide locking pathway 713 is positioned within the body 712 of the wire guide assembly 710 leading to a wire guide locking slot 715 for a wire guide The attachment mechanism 738 facilitates connection between the wire lock assembly 710 and an access port of a second medical device. In this embodiment, the attachment mechanism 738 is configured to engage with a port of an endoscope. As shown, the attachment mechanism 738 includes a groove 742 formed through the bottom section 714 of the wire lock assembly 710. A snap-fit locking mechanism 744 is provided within the groove 742 of the attachment mechanism 738 in order to provide for a more secure fit between the medical device and the port of the second medical device. A ledge 746, having a thickness with respect to the body 712 of the wire lock assembly 710, is positioned beneath the attachment mechanism 738. In this embodiment, the ledge 746 has a semi-hemispherical configuration and includes edges 747 which expand beyond the outer perimeter of the groove 742 of the attachment mechanism 738. The ledge 746 helps to prevent unwanted rotation of the wire lock assembly relative to a housing of the second medical device. The dimensions of the attachment mechanism 738 and the ledge 746 may be modified based on the dimensions of the second medical device. Within the groove 742 of the attachment mechanism 738 of the wire lock assembly 710 is an angled ramp 760. The angled ramp 760 allows the wire lock assembly 710 to be secured to a second medical device by sliding the wire lock assembly 710 onto a port of the second medical device.

The seal 740 is fluidly engaged with the central pathway 720 of the wire lock assembly 710 and is configured to limit the escape of any fluids that may be present within a working channel of a second medical device without inhibiting the insertion or movement of wire guides, catheters, or similar elongate devices. This configuration can be of particular benefit in preventing bodily fluids such as bile and blood from escaping and contaminating the physician and the working environment. The design and configuration of the seal 740, including the types of materials from which it may be manufactured, are well known to those skilled in the art. In this embodiment, the seal 740 is positioned between the bottom portion 714 and the intermediate portion 716 of the wire lock assembly 710. While an exemplary seal 740 may include a single slit, other types of slits, torn holes, arranged slits, or penetrable seals may alternatively be used. For example, other seal configurations include duckbill, membrane with slit (e.g., polystyrene, silicone, or another compliant polymer material), or other designs having the ability to seal around the catheter and wire guide to prevent any proximally migrating fluid from exiting the channel. The seal 740 in this embodiment is comprised of two generally flat surfaces. A notch 759 is present on a raised surface 756 located on the intermediate section 716 of the body 712 of the wire guide locking assembly 710.

Figure 32:
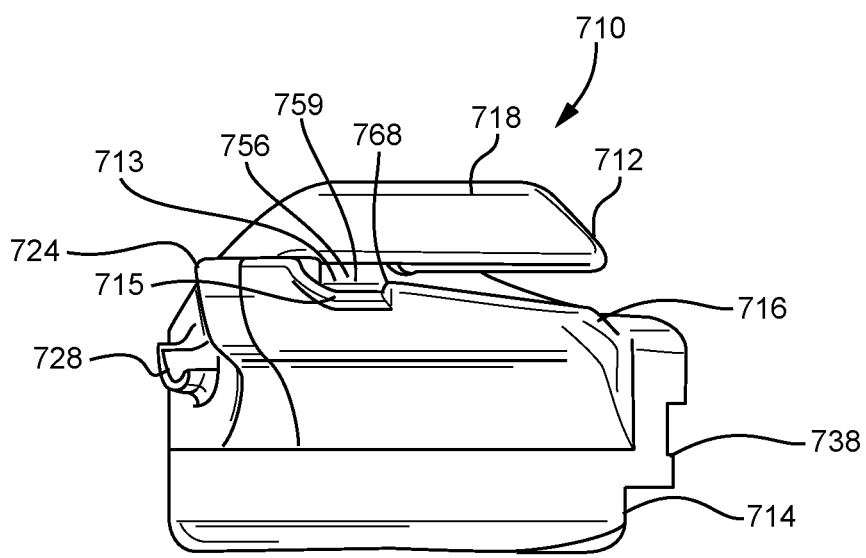
FIG. 32 illustrates a side view of an embodiment of a wire lock assembly for use with a secondary medical device.

FIG. 32 illustrates a side view of the wire guide assembly 710. As shown, the wire lock assembly 710 includes a wire guide locking slot 715, an attachment mechanism 738, and a wire guide tail lock 728. The wire guide locking slot 715 is present on a side wing 724 of the wire lock assembly 710. The wire guide locking slot 715 includes a snap-fit locking mechanism 768 that further facilitates locking of the wire guide. The top portion 718 and the intermediate portion 716 of the wire lock assembly form a wire guide locking path 713 leading to the wire locking slot 715. The wire guide locking path 713 includes a raised surface 756 that is positioned on the intermediate section 716 of the wire lock assembly. The raised rounded surface 756 extends about the periphery of the central pathway 720 and has a generally semi-hemispherical shape. A notch 759 is present on a raised surface 756 located on the intermediate section 716 of the body 712 of the wire guide locking assembly 710. The notch 759 is positioned in the non-linear pathway.

Figure 33:
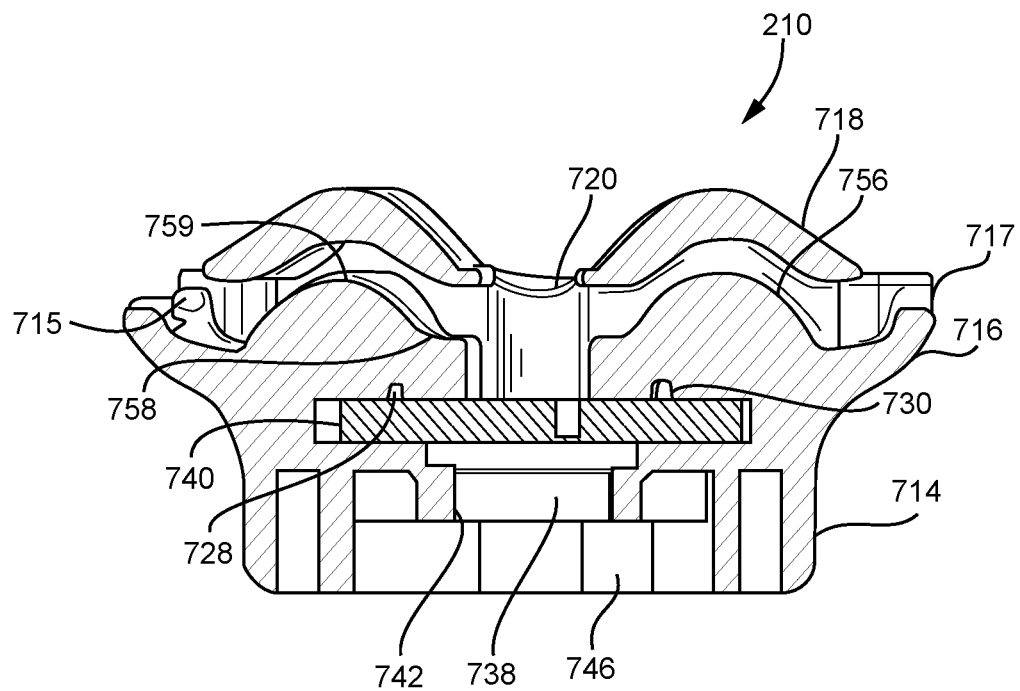
FIG. 33 illustrates a cross-sectional view of an embodiment of a wire lock assembly for use with a secondary medical device.

FIG. 33 illustrates a cross-sectional view of the wire guide assembly 710. As shown, the view is from the back of the body 712 of the wire guide assembly 710. The wire lock assembly 710 includes a central pathway 720, an attachment mechanism 738, and a seal 740 disposed within the body 712 of the wire lock assembly 710. The top portion 718 and the intermediate portion 716 of the wire lock assembly form a wire guide locking path 713 leading to the wire locking slot 715. The wire guide locking path 713 includes a raised surface 756 that is positioned on the intermediate section 716 of the wire lock assembly. The raised rounded surface 756 extends about the periphery of the central pathway 720 and has a generally semi-hemispherical shape. As shown, the raised rounded surface 756 includes a taper extending from central pathway 720 to the outer periphery of the intermediate section 716. The tapered section of the raised rounded surface 756 increases in diameter as it expands toward the outer periphery of the intermediate section 716. The raised rounded surface 756 includes a tapered, generally rounded surface that extends about the periphery of the intermediate opening. The wire lock assembly 710 further includes a flattened edge 758 positioned on the intermediate section 716 of the wire lock assembly. When the wire guide is secured in the wire guide locking slot 715, 717, the flattened edge 758 may be used as a wedge between the wire guide and the catheter when the user pulls upward on the catheter in order to perform a catheter exchange. A notch 759 is provided on the rounded surface 756 of the intermediate section 716 of the body 712 of the wire lock assembly 710. As shown, the notches are positioned along the wire guide locking path 713 and assist to prevent the wire guide from moving from the locked position within the wire guide locking slot 715, 717 inadvertently. Wire guide tail locks 728, 730 are positioned through the intermediate section 716 of the body 712 of the wire guide assembly. As shown in FIG. 33, the wire guide tail locks 728, 730 are in communication with the seal 740 and are positioned transverse to the central pathway 720 disposed through a portion of the intermediate section 716 of the body 712 of the wire lock assembly 710.

Figure 34:
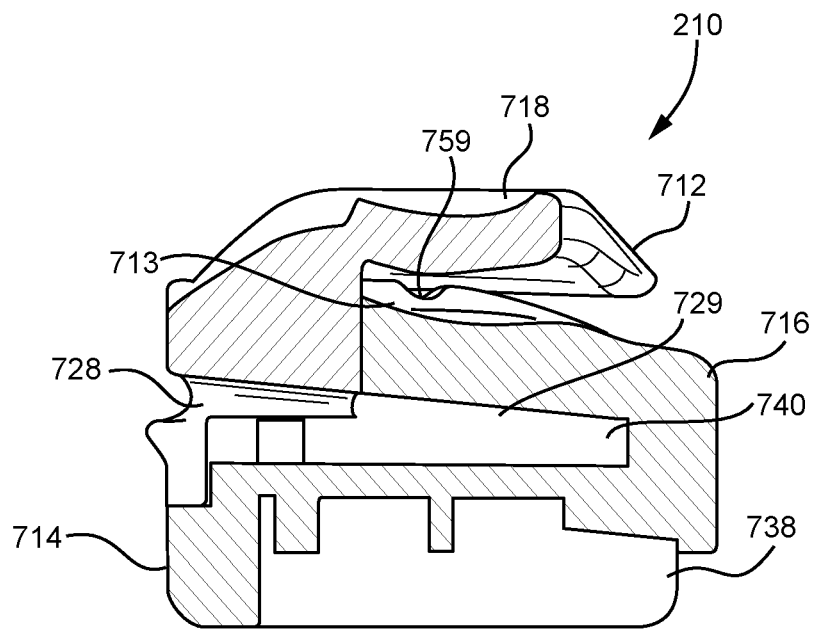
FIG. 34 illustrates a cross-sectional view of an embodiment of a wire lock assembly for use with a secondary medical device.

FIG. 34 illustrates a cross-sectional view of the wire guide assembly 710. As shown, the view is from a side of the body 712 of the wire guide assembly 710. The wire lock assembly 710 includes a central pathway 720, an attachment mechanism 738, and a seal 740 disposed within the body 712 of the wire lock assembly 710. The top portion 718 and the intermediate portion 716 of the wire lock assembly form a wire guide locking path 713 leading to the wire locking slot 715. A wire guide tail lock 728 is disposed through a portion of the intermediate section 716 of the body 712 of the wire lock assembly 710. In this embodiment, the wire guide tail lock 728 forms an angled pathway 729 that is in communication with the seal 740. The angled pathway 729 promotes engagement of a proximal end of a wire guide into contact with the seal 740 when the proximal end of the wire guide is placed in the wire guide tail lock 728. This engagement with the seal 740 locks the proximal end of the wire guide within the wire guide tail lock 728 and provides a tactile indication to the user that the proximal end of the wire guide is secured. A notch 759 is provided on the rounded surface 756 of the intermediate section 716 of the body 712 of the wire lock assembly 710. As shown, the notch 759 is positioned along the wire guide locking path 713 and assists to prevent the wire guide from moving from the locked position within the wire guide locking slot 715 inadvertently.

Figure 35:
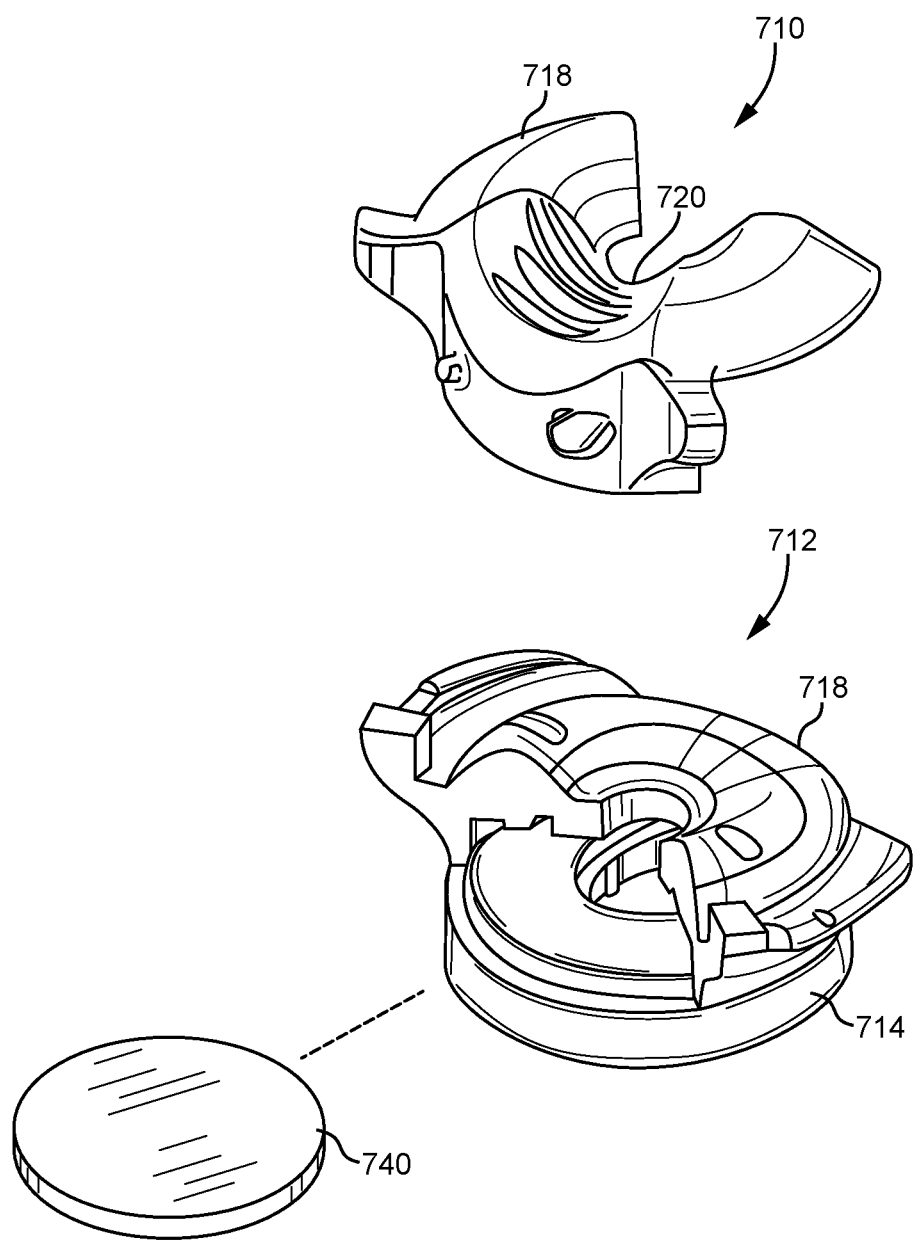
FIG. 35 illustrates an exemplary embodiment of a disassembled wire lock assembly.

FIG. 35 illustrates an exemplary embodiment of a disassembled wire lock assembly 710. The wire lock assembly 710 is formed of a suitable material such as plastic. The materials may be molded to a particular form, where the wire lock assembly 710 has a bottom section 714, intermediate section 716, and a top section 718. The seal 740 is provided within the body 712 of the wire lock assembly 710. In this embodiment, the seal 740 is secured between the intermediate section 716 and the bottom section 714 of the wire lock assembly 710 and in fluid communication with the central pathway 720 of the wire lock assembly 710. Although the exemplary embodiment illustrated here is constructed by three pieces snap fit together, the wire lock assembly 10 may be made from one or more pieces that may be affixed together in any way. For example, pieces may be ultrasonically bonded, heat bonded, glued together, or affixed in any other way.

Novel features of the disclosed medical device can be successfully used in a variety of applications. Indeed, the medical device disclose herein can be used in a vast number of widely differing medical procedures. In particular, the disclosed medical device can be used in medical procedures in which one or more elongate medical instruments such as a catheter or a wire guide needs to be secured relative to either a patient or another medical instrument.

Any other undisclosed or incidental details of the construction or composition of the various elements of the disclosed embodiment of the present invention are not believe to be critical to the achievement of the advantages of the present invention, so long as the elements possess the attributes needed for them to perform as disclosed. The selection of these and other details of construction are believed to be well within the ability of one of even rudimentary skills in this area in view of the present disclosure. Illustrative embodiments of the present invention have been described in considerable detail for the purpose of disclosing a practical, operative structure whereby the invention may be practiced advantageously. The designs described herein are intended to be exemplary only. The novel characteristics of the invention may be incorporated in other structural forms without departing from the spirit and scope of the invention. Indeed, different features of the disclosed embodiments can be integrated into a single structure, or alternatively, provided as separate pieces. For example, the disclosed embodiments may be paired with a second medical device, such as a tear down tool. The tear down tool may be coupled to the medical device through mechanical attachments including, but not limited to, the use of magnets, adhesives, snap-fit mechanisms, etc. Alternative arrangements may also be used in order to facilitate connection between the two devices.

The invention claimed is:

1. A wire lock assembly for an access port of an elongate medical tube, comprising
a body having an exterior surface, an interior surface, and a central opening disposed therethrough,
and at least one seal supported within the interior surface of the body in communication with the central opening, the seal comprising a passageway therethrough,
wherein the interior surface of the body defines a non-linear pathway in communication with the central opening for securing one or more medical devices, the non-linear pathway of the interior surface is defined by a plurality of bends positioned to distribute a force applied to at least one of the one or more medical devices secured within the non-linear pathway such that the at least one of one or more medical devices is automatically locked in position, wherein the at least one of the one or more medical devices traverses the entire non-linear pathway, and wherein the one or more medical devices assumes the non-linear pathway by bending.

2. The wire lock assembly of claim 1, further comprising an attachment mechanism disposed through the exterior surface of the body for attaching the wire lock assembly to the elongate medical device.

3. The wire lock assembly of claim 2, wherein the attachment mechanism comprises an open end and a closed end.

4. The wire lock assembly of claim 2, wherein the attachment mechanism comprises a U-shaped configuration.

5. The wire lock assembly of claim 1, further comprising at least one notch disposed in the body of the wire lock assembly.

6. The wire lock assembly of claim 5, wherein the at least one notch is disposed in the non-linear pathway.

7. The wire lock assembly of claim 1, wherein the body comprises a top section, intermediate section, and a bottom section.

8. The wire lock assembly of claim 7, wherein the non-linear pathway is disposed between the top section and the intermediate section of the wire lock assembly.

9. The wire lock assembly of claim 1, further comprising one or more seals positioned within the interior surface of the body.

10. The wire lock assembly of claim 1, wherein the wire lock assembly includes one or more tail lock passages disposed through the body of the wire lock assembly.

11. The wire lock assembly of claim 10, wherein the tail lock passages are disposed through the body of the transverse to the central opening.

12. The wire lock assembly of claim 11, wherein the tail lock passages have an angled interior surface.

13. A wire lock assembly, comprising
a body having an exterior surface, an interior surface, and a central opening disposed therethrough, and
one or more tail lock passages disposed through the body;
wherein the interior surface of the body defines a non-linear pathway formed between a top section and an intermediate section of the body in communication with the central opening for securing one or more medical devices, the non-linear pathway of the interior surface is defined by a plurality of bends positioned to distribute a force applied to at least one of the one or more medical devices secured within the non-linear pathway such that the at least one of one or more medical devices is automatically locked in position, wherein the at least one of the one or more medical devices traverses the entire non-linear pathway, and wherein the one or more medical devices assumes the non-linear pathway by bending.

14. The wire lock assembly of claim 13, wherein the one or more medical devices comprises a wire guide.

15. The wire lock assembly of claim 13, wherein the tail lock passages are disposed through the body of the transverse to the central opening.

16. The wire lock assembly of claim 15, wherein the tail lock passages have an angled interior surface.

17. The wire lock assembly of claim 13, further comprising an attachment mechanism disposed through the exterior surface of the body for attaching the wire lock assembly to the elongate medical device.

18. A system for holding a wire guide, comprising:
an endoscope having an access port;
a wire lock assembly affixed to the access port, the wire lock assembly comprising a body having an exterior surface, an interior surface, and a central opening disposed therethrough and at least one seal supported within the interior surface of the body in communication with the central opening, the seal comprising a passageway therethrough;
wherein the interior surface of the body defines a non-linear pathway in communication with the central opening for securing one or more medical devices, the non-linear pathway of the interior surface is defined by a plurality of bends positioned to distribute a force applied to at least one of the one or more medical devices secured within the non-linear pathway such that the at least one of one or more medical devices is automatically locked in position, wherein the at least one of the one or more medical devices traverses the entire non-linear pathway, and wherein the one or more medical devices assumes the non-linear pathway by bending.

* * * * *